(12) United States Patent
Chalasani et al.

(10) Patent No.: US 6,482,413 B1
(45) Date of Patent: Nov. 19, 2002

(54) VITAMIN $B_{12}$ —BIODEGRADABLE MICRO PARTICULATE CONJUGATE CARRIER SYSTEMS FOR PERORAL DELIVERY OF DRUGS, THERAPEUTIC PEPTIDES/ PROTEINS AND VACCINES

(75) Inventors: Kishore Babu Chalasani, Hyberabad (IN); Vamanrao Diwan, Hyderabad (IN); Kondapuram Vijaya Raghavan, Hyderabad (IN); Gregory John Russell-Jones, Roseville (AU); Sanjain Kumar Jain, Sagar (IN); Kollipara Koteshawar Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/795,979
(22) Filed: Mar. 1, 2001
(51) Int. Cl.$^7$ .................. A61K 39/385; A61K 31/70
(52) U.S. Cl. ................................ 424/194.1; 514/52
(58) Field of Search ................... 424/194.1; 514/52

(56) References Cited

U.S. PATENT DOCUMENTS

| | | | |
|---|---|---|---|
| 5,540,064 A | * | 7/1996 | Matsuda et al. |
| 5,574,018 A | * | 11/1996 | Habberfield et al. |
| 5,589,463 A | * | 12/1996 | Russell-Jones et al. |
| 5,807,832 A | * | 9/1998 | Russell-Jones et al. |

* cited by examiner

Primary Examiner—Hankyel T. Park
(74) Attorney, Agent, or Firm—Foley & Lardner

(57) ABSTRACT

The invention relates to a novel complex for oral delivery of drugs, therapeutic protein/peptides and vaccines which are loaded in a Vitamin $B_{12}$ ($VB_{12}$) coupled particulate carrier system with spacers in between, the carrier system with spacers having a formula $VB_{12}$—R'/R"—N wherein, R' or R" is spacer and/or agents for derivatization of $VB_{12}$ to provide either $NH_2$ or COOH or SH groups, and N is the micro or nano particle carriers for the delivery of injectable drugs, therapeutic protein/peptides and vaccines.

31 Claims, 11 Drawing Sheets

Legend:
D-injectable drug
SP-long chain spacer to retain
IF affinity of Vit. B12 and/or for
ease of coupling
BDC-bio-degradable carrier
particle (microsphere/nanoparticle)

FIG. 1

Legend:
D-injectable drug
SP-long chain spacer to retain IF affinity of Vit. B12 and/or for ease of coupling
BDC-bio-degradable carrier particle (microsphere/nanoparticle)

1) DSN1   = NH NH-(CH2)2CONH(CH2)2-S-S-(CH2)2-NH eVB12
2) DCN1   = NH (CH2)6-NH eVB12
3) DGN1   = NH (CH2)2 S-S- (CH2)2 NH- eVB12
4) DSN2   = NH- CH2 (OH)-CH-CH2-NH eVB12
14) DDN2  = (CH2)12 -5'OVB12
5) DSN3   = NHNHeVB12
10) DDM3  = (CH2)12 - 5'OVB12
8) DSM1   = NH(CH2) 6NHeVB12

Earlier patents:

VB12 – bioactive (Covalent complex)

↓

Different dosage forms

This patent:

Legend:
D-Bioactive
SP-long chain spacer to retain
IF affinity of Vit. B12 and/or for
ease of coupling
BDC-bio-degradable carrier
particle (microsphere/nanoparticle)

Different dosage forms

VITAMIN B$_{12}$ — BIODEGRADABLE MICRO PARTICULATE CONJUGATE CARRIER SYSTEMS FOR PERORAL DELIVERY OF DRUGS, THERAPEUTIC PEPTIDES/ PROTEINS AND VACCINES

FIELD OF THE INVENTION

This invention relates to a complex for oral delivery of drugs, therapeutic protein/peptides, vaccines, which are loaded in Vitamin B$_{12}$ coupled particulate carriers system with spacers in between. Typically, VB$_{12}$ acts as ligand for endocytosis through intestine and the particulate systems will act as a cargo protecting the intestinal labile drugs to deliver them to systemic destination and/or to the specific site required.

BACKGROUND ART

Although many peptide/proteins, pharmaceuticals and vaccines are currently administered by injection, this method of delivery has a number of disadvantages which has led the scientific community to strive to develop an alternative oral delivery system for these bioactives. The inherent limitations to parenteral delivery include (1) patient compliance (there is a need for repeated injections due to the short half-life of these molecules) (2) discomfort from this form of delivery caused by the need for repeated prolonged dosage regimen (3) highly variable bioavailability both within and between subjects for molecules such as subcutaneous insulin and (4) the non-physiological delivery pattern particularly of subcutaneous injections. Further, small increases in actual drug delivered due to changes in dosage and/or mode of delivery may cause down-regulation of the desired response to most of these bioactives. In contrast most often a pulsatile or flat delivery profile is required which mimics the normal physiological rhythm. Apart from the problem described, parenteral vaccines are of limited efficacy due to the need for repeated vaccination and due to the fact that they elicit only humoral immunity.

To address the above problems, various non-invasive delivery systems have been attempted. The major delivery barriers common to these routes are (1) poor intrinsic permeability due to large size and hydrophilicity of the bioactive (2) enzymatic degradation in the hostile environment of GIT by lumenal proteases and cellular peptidases, unlike some of the traditional drugs. Although these odds are formidable for the per oral route, it enjoys advantages in terms of convenience and patient compliance as well as safety, less stringent quality control, cost of therapy and for vaccines, the potential for unlimited frequency of boosting. Furthermore, oral vaccines offer the potential to protect against not only enteric pathogens (by producing localized sIgA), but also a wide range of pathogens infecting other mucosa (respiratory and genital) by producing a common disseminated mucosal immune response. Furthermore oral vaccines may prove particularly useful in the elderly because mucosal immunity, unlike systemic immunity does not seem to be an age associated dysfunction. This mode of immunization may also be beneficial in the very young, because mucosal immunity develops earlier in ontogeny than systemic immunity. Over the past few decades significant efforts have been made to develop oral protein/vaccine systems using permeation enhancers (ZOT, which has proven to be toxic on long term use), enzyme inhibitors, surfactants, emulsions, colon targeted systems, bioadhesive systems and particulate systems. Although the challenges to develop oral systems are numerous, the potential therapeutic need remains high, particularly with increased identification of novel peptides and increased production of existing protein drugs from the biotechnology arena.

Peptide/protein drugs and vaccines are mostly given by parenteral routes. The problems for the oral delivery are:

1) Degradation of the above bioactives in the harsh environment of intestine and by gut proteases.
2) Their large size and hydrophilicity causes permeability problem across the intestine.
3) The fragility of these bioactives precludes to be formulated as oral dosage forms.
4) And finally their short in-vivo half lives.

Over the past 3–4 decades efforts have been made to deliver them by oral route using various formulation approaches such as emulsions, microspheres, nanoparticles, vasicular carriers such liposomes, using permeation enhancers and protease inhibitors and by protein-carrier conjugates.

Recently it has been shown that the problem of poor intrinsic permeability can be possibly overcome by delivery via a specific carrier mechanism that transports pharmaceuticals from the intestine into the circulation. In this regard, Russell-Jones and co workers [1994] have found the possibility of coupling these bioactives with Vitamin B12 (VB$_{12}$) in a manner that does not interfere with intrinsic factor (IF) mediated uptake of the VB$_{12}$ carrier to the systemic circulation. Some interesting results have been achieved with oral VB$_{12}$ conjugates of LHRH (Russell-Jones 1998), interferon (Habberfield and Jensen-Pippo PPO, 1996) G-CSF and erythropoietin (Habberfield, 1996). However, such successful oral delivery of conjugates cannot be obtained with many other bioactives because of the limited uptake of VB$_{12}$ (1 nmol/dose), the loss of bioactivity due to covalent linkage, loss of IF affinity of VB$_{12}$ (steric factor) and finally the liability of such conjugates to GIT degradation. To address the above problems we have made endeavors to make an oral delivery system (VB$_{12}$-sphere conjugate) that could be targeted to the systemic circulation through VB$_{12}$-IF-IFR ligand-mediated endocytosis via ileocytes of the intestine following oral administration. In vitro transport of VB$_{12}$ coated polystyrene nanoparticles (non-biodegradable, hydrophobic) has been demonstrated across Caco-2 cell cultures (Russell Jones, 1997, 1999). However, the level of transport cannot be extended to other polymeric particulates in general. This can be explained by the differing physicochemical characteristics of polymers such as hydrophobicity, as hydrophobic materials may be more readily taken up by cell surface lipid bilayers. Also one of the prerequisites for drug delivery is that the polymer used to make the nanoparticles should readily or slowly be degraded in the systemic environment or by enzymes which release the pharmaceutical molecule and thereby initiate its bioactive response. Hence, the use of nonbiodegradable polymers for transport studies is not necessarily indicative, of uptake by other biodegradable polymers in general. Further, developing a system of loading of hydrophilic peptide/protein or vaccine bioactives into hydrophobic polymeric carriers is definitely not obvious.

Among all these approaches, there was some enhancement of delivery, but major break through of achieving therapeutically relevant dose delivery is not achieved. In the recent past, a delivery system was invented by one of the co-inventors using VB$_{12}$ as carrier molecule which is coupled with protein drug to be delivered i.e. VB$_{12}$-protein conjugates. VB$_{12}$ binds with intrinsic factor of the intestine (VB$_{12}$+IF→VB$_{12}$ IF) in the duodenum and the whole VB$_{12}$ IF complex binds to intrinsic factor receptor (IFR) at the ileum of the small intestine. From there, it is endocytosed and subsequently transcytosed by transcobolamin (TcII) to reach systemic circulation.

Therefore, if protein is coupled with VB$_{12}$, it will be co-transported along with VB$_{12}$ molecule to reach systemic circulation.

Two conditions are to be satisfied for this approach i.e.

Case 1: $VB_{12}$ molecule must retain its IF affinity after being coupled to protein to be delivered.

Case 2: Also protein molecule must retain its bioactivity after coupling to $VB_{12}$.

For case 1: Native $VB_{12}$ (cynocobolainin) cannot be directly coupled to protein, i.e. $VB_{12}$ losses its IF affinity by such coupling.

Therefore, in the above technology $VB_{12}$ is hydrolyzed, where it forms 3 isomers (a, b and e isomers). Among the 3 isomers, the 'e' isomer retains considerable IF affinity after coupling to other molecules.

Case 2: For the ease of coupling to provide suitable groups and to retain full bioactivity of protein drug, various derivatives of e-$VB_{12}$ using various spacers. These derivatives are coupled to protein drugs to be delivered. Such spacers also increases IF affinity of e isomer. About this technology, one of the inventors of the present application namely Dr. Gregory Russell Jones written a chapter in a book in 1995 (peptide based drug design Chapter 8). In this chapter, the author elaborated this technology and summarized the results of VB-LHRH analogs and $VB_{12}$ vasopressin and also mentioned the possibility of conjugating other bioactives such as EPO and G-CSF. Later in 1995, two research papers appeared in bioconjugate chemistry (1) $VB_{12}$-LHRH analogs (Volume 6, No. 1, 1995, 34–42), (2) $VB_{12}$-EPO and $VB_{12}$-G CSF (Volume 6, No.4, 1995, 461–465). Later in 1996, one of the authors patented $VB_{12}$-EPO and $VB_{12}$-G CSF conjugates (U.S. Pat. No. 5,480,68, August 1998. In this patent he claimed any derivative of $VB_{12}$ which retains IF affinity after being coupled protein drug to be delivered. Later, in November 1996 there is another patent (U.S. Pat. No. 5,574,018) on the similar system (Habber Field, who is associated D. Russell on some research paper works earlier) i.e. $VB_{12}$-EPO, $VB_{12}$-G SCF and $VB_{12}$-Interferon. But the derivative used is different i.e. at hydroxy site of ribose of $VB_{12}$. This derivatization at this site and derivatives coupled to protein drug also retain IF affinity of $VB_{12}$. But in the earlier patent any derivative of $VB_{12}$, which retains IF affinity after being coupled to protein drugs is claimed. Protein drugs used in the other patent are also same with exception of interferon.

Two U.S. Pat. Nos. 5,589,463 and 5,807,832 wherein, the one of the coinventor of the present application is also main inventor describe $VB_{12}$-bioactive chemical (covalent) conjugate. The bioactive may be protein, vaccine or antigen (may be of polysaccharide nature) or other biopharmaceutical (heparin) or traditional drug (neomycin). The above chemical complexes they claim to formulate in known dosage forms suitable for oral delivery gels, dispersions, emulsions, capsules, tablets etc. Technology of both these patents is somewhat similar to other patents, U.S. Pat. Nos. 5,548,064 and 5,574,018, which are, referred above.

In spite of all these, the conjugates of $VB_{12}$ have the following drawbacks.

1) Protein is not protected from degradation by proteases in gut.
2) All proteins cannot be coupled, as some protein bioactives may loose active molecular confirmation due to its coupling to bulky $VB_{12}$ (steric factors).
3) Uptake of $VB_{12}$ transport system (1 nano gram g/dose) is not sufficient for proteins which have very short half lives i.e. therapeutically relevant dose cannot be achieved.

The present invention is entirely different in that bioactive (protein/vaccine or drug) is not directly coupled to $VB_{12}$ or its analogue. Instead, $VB_{12}$ or its analogues are covalently coupled to micro/nano particle surface in which bioactive is loaded. The micro and nano particles are made up of biodegradable and pharmaceutically acceptable polymers.

DETAILED DESCRIPTION OF THE INVENTION

The conjugation of various peptides and proteins to the Vitamin $B_{12}$ molecule has been shown to facilitate the in-vitro and in-vivo transport of these moieties across the epithelial cells of the intestine. However, pharmaceutically relevant oral delivery of many vitamin $B_{12}$-pharmaceutical conjugates does not occur with many of these bioactives due to the limited uptake capacity of the $VB_{12}$ transport system, loss of bioactivity of native protein during conjugation to $VB_{12}$, loss of intrinsic factor (IF) affinity of the conjugates and finally due to the liability of the bioactives to GI degradation. In order to overcome these shortcomings we have endeavoured to develop vitamin B12-particulate (both microspheres and nanospheres) systems that could be taken up by the natural uptake mechanism for $VB_{12}$. Different biodegradable particulate systems (microspheres and nanospheres) were prepared. These particles were surface modified with vitamin $B_{12}$ and these preformed sphere conjugates were loaded with therapeutic proteins (insulin, hepatitis 'B' vaccine). In some cases the loading step was altered. In-vitro studies showed that insulin was protected from degradation by gastric enzymes. These systems, of different sizes, were fed to diabetic rats, whose blood glucose levels were monitored over time. The pharmacological bioavailability of these systems was 5–25%, which showed not only oral bioactivity but also evidence of controlled release of these biopharmaceuticals. These systems showed interesting results with vaccine loaded $VB_{12}$ microspheres and nanospheres. Thus the above carrier system and various strategies mentioned herein, upon further testing and optimization, may make per oral protein delivery a reality.

The present invention relates to the field of pharmaceutical preparation of traditional injectable drugs given parenterally, peptide and protein pharmaceuticals including vaccines, particularly in the field of such pharmaceutical preparations, which are suitable for oral delivery.

In accordance with the present invention there is provided a drug delivery system comprising a protein drug (insulin and hepatitis 'B' vaccine) incorporated within the biodegradable polymeric particulates, which are coated with $VB_{12}$ on their surface as shown in FIG. 1, wherein D is the injectable drug, SP- is the long chain spacer to retain IF affinity of Vitamin $B_{12}$ and/or for ease of coupling, BDC is the biodegradable carrier particle (microsphere/nano particle).

For the purpose of successful oral drug delivery, $VB_{12}$ acts as targeting ligand for initial transport across the intestinal epithelium the circulation or for site-specific delivery of the vaccines. The $VB_{12}$ carries the particulate spheres (micro and nano) along with it until the desired site reached.

In the embodiment of the present invention, $VB_{12}$-microsphere and $VB_{12}$-nanoparticle systems deliver the traditional parenteral drugs, peptides/proteins including vaccines by oral route. Various biodegradable microspheres and nanoparticies are prepared with existing natural, semi synthetic and synthetic polymers. These particulates systems (micro and nano) can be surface modified to provide groups suitable for $VB_{12}$ conjugation.

Vitamin $B_{12}$ derivatives or their various derivatives with numerous spacers (Russell Jones et al 1995a and 1995b) were coupled to particulate carriers. Different linkages, both biodegradable (cleaved by systemic enzymes) and non-biodegradable covalent linkages are used to link the $VB_{12}$ to the particulate. The coupling also involves ionic, coordinate covalent. and strong physical adsorptive bounds.

In an embodiment, the drugs to be delivered are the traditional drugs administered exclusively by parenteral routes, therapeutic peptides/proteins, other biopharmaceuticals such as heparin and vaccines for immunization.

In another embodiment of the present invention, the drugs to be delivered are the traditional drugs administered exclusively by parenteral routes selected from gentamycin and Amikacin, therapeutic peptides/proteins selected from insulin, EPO, G-CSF, GM-CSF, Factor VIR, LHRH analogues and Interferons, other biopharmaceuticals such as heparin and vaccines selected from Hepatitis 'B' surface antigen, typhoid and cholera vaccine for immunization.

In yet another embodiment, the carrier system is a pharmaceutically acceptable carrier comprising $VB_{12}$ or its analogs or their derivatives to be coupled to biodegradable polymeric particulate carriers, which are, loaded with drugs/vaccines given parentally.

In yet another embodiment, the carrier system is transcytosed after receptor mediated endocytosis at or around ileum by the natural uptake $VB_{12}$.

In yet another embodiment, $VB_{12}$ is the targeting ligand for the intestine to systemic and/or lymphatic destiny.

In yet another embodiment, $VB_{12}$ is native cynocobalamine ($VB_{12}$) or various analogs of $VB_{12}$ viz., aquocobalimin, adenosylcobalamin, methylcobalamin, hydroxycobalamin and/or their derivatives or alkylcobalamines in which alkyl chain is linked to cobalt of $VB_{12}$ or cynocobolamin with chloro, sulphate, nitro, thio or their analide, ethylamide, propionamide, monocarboxylic and dicarboxylic acid derivatives of $VB_{12}$ and its analogues or monocarboxylic, dicarboxylic and tricarboxylic acid derivatives and prominamide derivatives of 'e' isomer of monocarboxy $VB_{12}$ and analogues of $VB_{12}$ in which cobalt is replaced by other metals (zinc or nickel etc) and various spacers attached to these derivatives or any derivatives which retains IF affinity after coupling to biodegradable particulate carriers.

In yet another embodiment, the derivatives of $VB_{12}$ also include derivatization at primary 5'-hydroxyl and 2-hydroxyl groups of ribose moiety of $VB_{12}$ and various spacers attached at this site useful for coupling with particulate carriers.

In yet another embodiment, R'–R"- the spacers and/or agents for derivatization of $VB_{12}$ to provide either $NH_2$ or COOH or SH groups and combination thereof are selected from diacids or alkyl diacids (COOH—COOH, (COO $(CH_2)_n$COO)) alkyl diamines ($NH_2(CH_2)n$—$NH_2$) or alkyl diamides (NHCO (CH)n $CONH_2$) or hydrazides ($NH_2NH_2$) or alkyl dihydrazides ($NH_2NHCO(CH_2)n$ $CONHNH_2$ or substitution SH group containing agents (N-succinymnidyl3-(2-pyridyldithio)propionate or its long chain alkyl derivatives or acid anhydrides [(CH)n COCOO)] or acid halide spacers (R$(CH_2)n$ COCl) or anhydroxy activated ester functional groups (NHS) which are used for the peptide bonds or surfactant derivatives or polymeric spacers, and in all cases 'n' is an integer from 1,2,3 . . . infinite.

In yet another embodiment, the microspheres or nanoparticles are made up of biodegradable and pharmaceutically acceptable polymers.

In yet another embodiment, the drug loaded polymeric particulates degrade in-vivo to release and deliver a protein pharmaceutical/vaccine for its bioactive response.

In yet another embodiment, the particulate carriers are biodegradable, hydrophobic or hydrophilic polymeric microspheres/nanoparticles containing surface COOH, anhydride, $NH_2$, SH groups and combination thereof.

In yet another embodiment, the particulate carriers systems are of both monolithic (matrix type, cross-linked) and/or reservoir type (microcapsule and nanocapsule or multi particulate type (particles within the particles) or particles formed by co-addition the ligand $VB_{12}$ to the polymer i.e., conjugate polymer particulates.

In yet another embodiment, the particulate carriers include polysaccharide polymers viz., starch and their derivatives, pectin, Amylose, guar gum and their derivatives, dextran of different molecular weights and their derivatives, chitosan and their derivatives, chondriotan sulphate and their derivatives and finally other natural and semi synthetic derivatives of polysaccharides and such polymers thereof.

In yet another embodiment, the cross linking agents for polysaccharides include epichlorohydrin, $POCl_3$, borax (guar gum), aldehydes (e.g., glutaraldehyde) and other cross linking agents thereof which cross links polysaccharide polymers to give particulate carriers.

In yet another embodiment, less hydrophilic to hydrophobic particulate carriers include biodegradable polymers of poly(methylmethacrylate), poly(hydroxybutyrate), polylactide(coglycolic acid), poly(anhydride) microspheres of (fumaric acid: sebacic acid and poly fulmaric acid) and poly (lactide co-glycolide), fatty acylated particulates (hydrophilic core surrounded by fatty acyl layer), LDL carriers, multiparticulate systems (polymeric particles encapsulated in polymers of different hydrophilicity or hydrophobicity) and finally different compositions of these polymers.

In yet another embodiment, the particulate carriers also include natural protein polymers such as albumin, gelatin, semi synthetic or peptide based synthetic polymers and derivatives thereof.

In yet another embodiment, the cross-linking agents such as terephthloyl chloride, glutaraldehyde and such cross linkers which cross-links protein polymers to give particulate carriers.

In yet another embodiment, the particulates, which are formed by polymerization of monomers such as glutaraldehyde to poly (glutaraldehyde), and such particles formed by polymerization of monomers and their coupling to $VB_{12}$.

In yet another embodiment, the size of the system for the systemic delivery of drugs, proteins and vaccines are ranging from few nanometers to 10 $\mu$m or more.

In yet another embodiment, these particulate systems which are modified or activated on the surface to suit $VB_{12}$ linkage and/or complexation.

In yet another embodiment, the particulate system is surface modified with $VB_{12}$, and includes coupling of $VB_{12}$ to biodegradable particulate carriers.

In yet another embodiment, coupling of $VB_{12}$ derivative and particulates include both biodegradable and non biodegradable bonds with and without spacers in between.

In yet another embodiment, coupling between $VB_{12}$ derivative and particulate carriers or surface modified/activated particulates is by amide bond with carbodiimides such as 1-ethyl 3-3dimethyl amino propyl carbodiimide (EDAC) or 1,1' carbonyl diimidazole (CDI) or N,N' diisopropyl carbodiimide (DIPC) and other peptide coupling agents or N-hydroxy succinmide activated coupling (NHS) or periodate coupling or glutaraldehyde activated coupling or CNBR mediated coupling or acid halide induced amide coupling or by the use of hydrophilic spacer ethylene glycol bis(succinimidyl succinate) (EGS) or hydrophobic spacers disuccininidyl suberate (DSS) or via a thiol cleavable spacer with N-succinimidyl 3-(2-pyridyldithio) propionate (SPDP) and any such conjugates which retains IF affinity for $VB_{12}$.

In yet another embodiment, the coupling involves physical adsorptive type or complexation.

In yet another embodiment, the drugs, therapeutic peptides/proteins and vaccines are entrapped within the highly dense $VB_{12}$ coupled biodegradable particulate carriers.

In yet another embodiment, the loading step of the bioactive agent in question is in the preformed particulate carrier conjugate or within the carrier during the preparation of the particulate spheres or during the coupling between the particles and $VB_{12}$ derivative.

In yet another embodiment, the bioactives to be delivered are 1) physically entrapped with in the particles before/after/ or during the conjugation or 2) adsorbed or 3) covalently coupled or 4) by ionic interaction or 5) complexation and any other methods there off to load $VB_{12}$ particulate systems.

In yet another embodiment, the use of surfactants, aggregation minimizers, protease inhibitors and permeation enhancers as adjuvants in the formulations.

In yet another embodiment, the delivery systems are co-administered with exogenous intrinsic factor (IF) of $VB_{12}$, especially for IF deficient species.

In yet another embodiment, the said delivery systems are formulated into dosage forms suitable for oral delivery.

In yet another embodiment, the oral dosage forms include solutions, suspensions, gels, pastes, elixirs, viscous colloidal dispersions, tablets, capsules and/or oral control release types and finally any such delivery forms for oral route.

Oral delivery of peptide and proteins has proven an elusive target for the pharmaceutical industry over the past few decades. In the present invention a model therapeutic protein, insulin and vaccine hepatitis 'B' vaccine were selected as model protein. The presence of various groups on $VB_{12}$ derivatives were assigned by comparing IR spectra with that of native $VB_{12}$. The 'e' carboxylate of $VB_{12}$, which has highest affinity for IF affinity, was separated and covalently linked to various spacers to give various $VB_{12}$ derivatives (FIG. 2). Various $VB_{12}$ particulate systems of different sizes were prepared and their surface was modified by various means to suit $VB_{12}$ conjugation (sizes were illustrated in the text). These $VB_{12}$ coupled particulate systems (FIG. 1) were loaded with insulin and hepatitis 'B' vaccine. It is assumed, even if some of the carrier systems delivers sub therapeutic doses of protein (insulin), its relevance would be adequate to trigger immune response. Consequently the problem is far less complicated for traditional drugs that are exclusively given parenterally (hence model drug was not chosen) and will be loaded at a later stage. For these studies permeation enhancers were not taken along with delivery systems, as the main objective is to study uptake mechanism of this carrier system. It is assumed that the above additives may probably potentiate the efficacy of the carrier system by allowing absorption through other mechanisms. In-vitro enzymatic study showed that insulin was protected against digestive action of intestinal enzymes when entrapped within the spheres, whereas free insulin solutions were completely degraded under the same experimental conditions (FIG. 3). Various nanoparticles $VB_{12}$ conjugates in the size range of 160–250 nm showed interesting results with model protein insulin. Antidiabetic activities of some representative insulin delivery systems are shown in FIGS. 4–8. These systems showed maximum blood glucose reduction of 48.4±4.1 (% initial) at 5 hours. The onset of action was observed 2 hours after administration for all the delivery systems. Maximum % decrease in glucose level (tmax) was found at the 5th hour for all the systems microparticulate conjugates, which was maximal at the 6th hour. The above results show similar uptake kinetics to that observed for $VB_{12}$ absorption in the rat, and suggest that the uptake be due to specific $VB_{12}$ mediated absorption, which takes several hours. During preliminary assessment of the different systems the duration of action was studied for 7 hours for all the systems (n=3 animals), but in later studies the uptake was continued for up to 12 hours (n=5) (FIG. 9). The Antidiabetic activity of plain insulin was estimated following intravenous (IV) and subcutaneous administration (FIG. 10). The pharmacological availability was assessed by the above results. The $AUC_{0-7}$ values were significantly higher (p<0.01) for nanoparticle conjugates and higher size nanoparticle conjugates (p<0.05) when compared to $AUC_{0-7}$ value for i.v. route. With microparticulate conjugates there was little difference in AUC's when compared to i.v. route but there was reduction in blood glucose levels at 3rd, 4th, 5th and 6th hours whereas i.v. injection of insulin showed no activity at these times. The pharmacological availability of various particulate conjugates was from 5% to as much as 23%. It is expected that microparticle conjugates may give good results with vaccines for mucosal immunity, as dose to trigger immune response will not be more than therapeutic proteins (work with hepatitis 'B' is under progress. Nanoparticle conjugates containing 10 I.U./kg showed best results. Uptake studies showed that the absorption is a $VB_{12}$ specific carrier-mediated type (FIG. 9). This carrier system and the various strategies described in the present invention have potential to replace the current need for injectable protein drugs/vaccines and other traditional drugs that are given exclusively by parenteral route. These preliminary findings provide a sound platform for further testing and optimizing a delivery technology for peroral delivery of injectable drugs.

For ease of understanding, the distinction between the instant invention and the prior art is schematically represented in FIG. 11. As shown therein, FIG. 11(A) represents the prior art wherein $VB_{12}$, a bioactive covalent complex is formulated as solutions or as dispersion or as paste or used as tablets, in appropriate dosage forms, FIG. 11(B) represents the instant invention wherein $VB_{12}$ or its analogues are covalently coupled to microsphere/nanoparticle surface in which bioactive ingredient is loaded and formulate dosage forms.

For easier understanding of this present invention, schematic representation of earlier patents and the present invention is shown in FIG. 11 wherein the Vitamin $B_{12}$ is covalently linked to the bioactive materials and administered as a solution, dispersion, paste and tablet forms. In the present invention, bioactive (protein/vaccine or drug) is not directly coupled to Vitamin $B_{12}$ or its analogues, instead Vitamin $B_{12}$ or its analogues are covalently coupled to microsphere/nanoparticle surface, in which bioactive ingredient is loaded and formulate dosage forms. The micro and nano particles are made up of biodegradable and pharmaceutically acceptable polymers.

As shown in FIG. 11, D is bioactive material, SP is long chain spacer to retain IF affinity of Vitamin $B_{12}$ and/or for case of coupling BDC is biodegradable carrier particle (microsphere/nanoparticles) and $VB_{12}$ is Vitamin $B_{12}$.

BRIEF DESCRIPTION OF THE DRAWINGS

FIG. 1 shows $VB_{12}$ coupled particulate systems.

Figure 2:
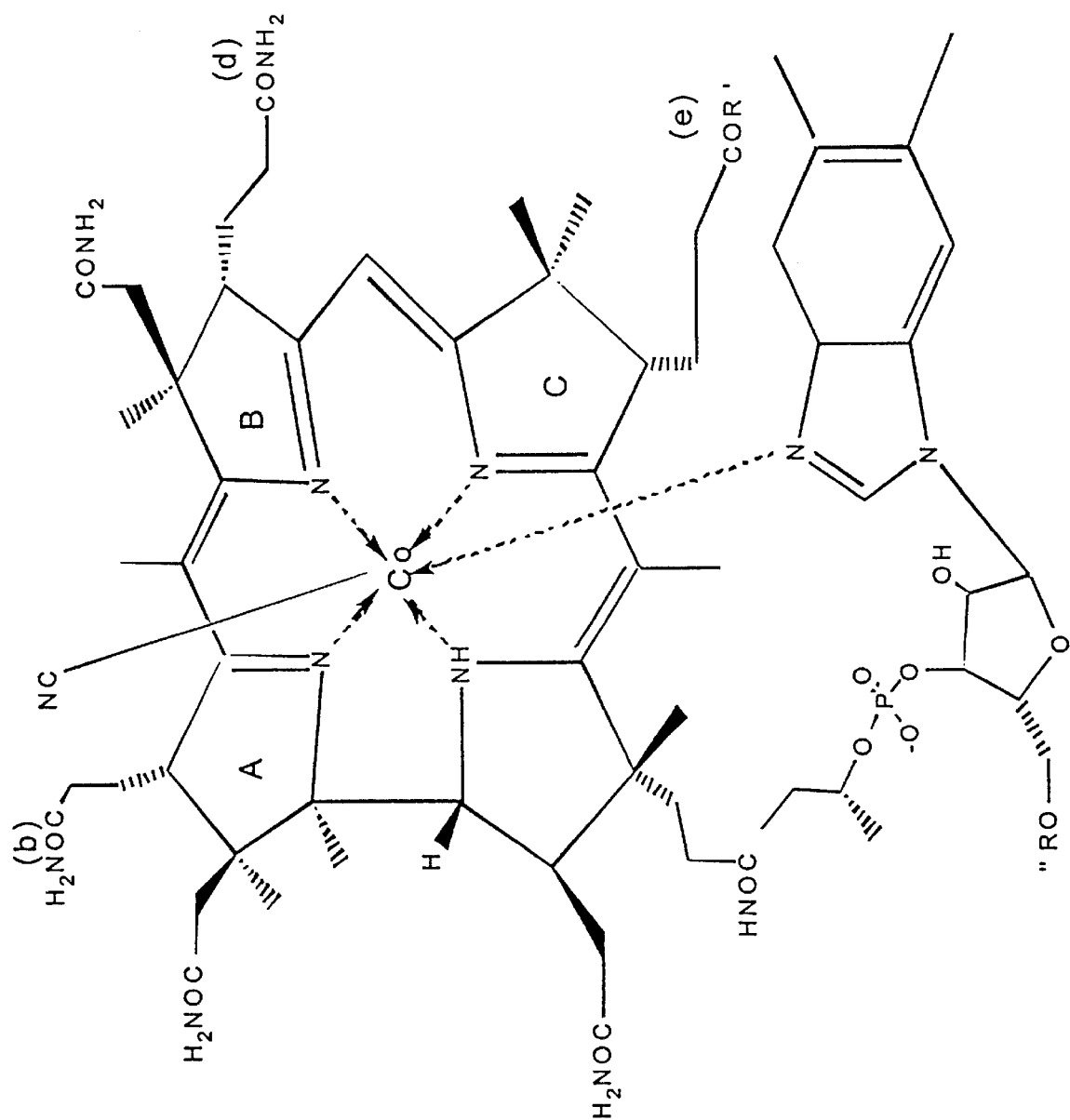
FIG. 2 shows structure of $VB_{12}$ and sites of linkage for IF affinity.
Figure 3:
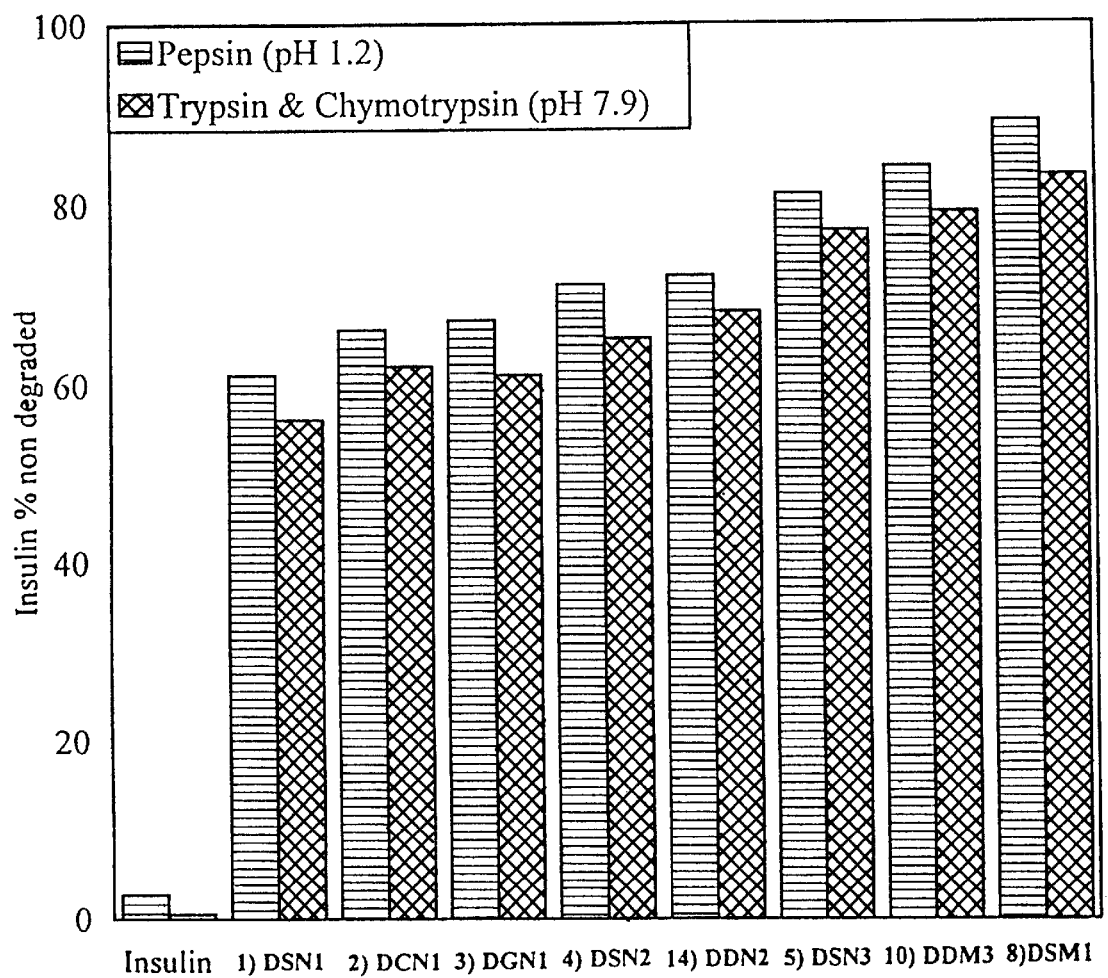
FIG. 3 graphical representation which shows effect of pH and proteolysis on plain insulin and insulin containing $VB_{12}$ microsphere conjugates.
Figure 4:
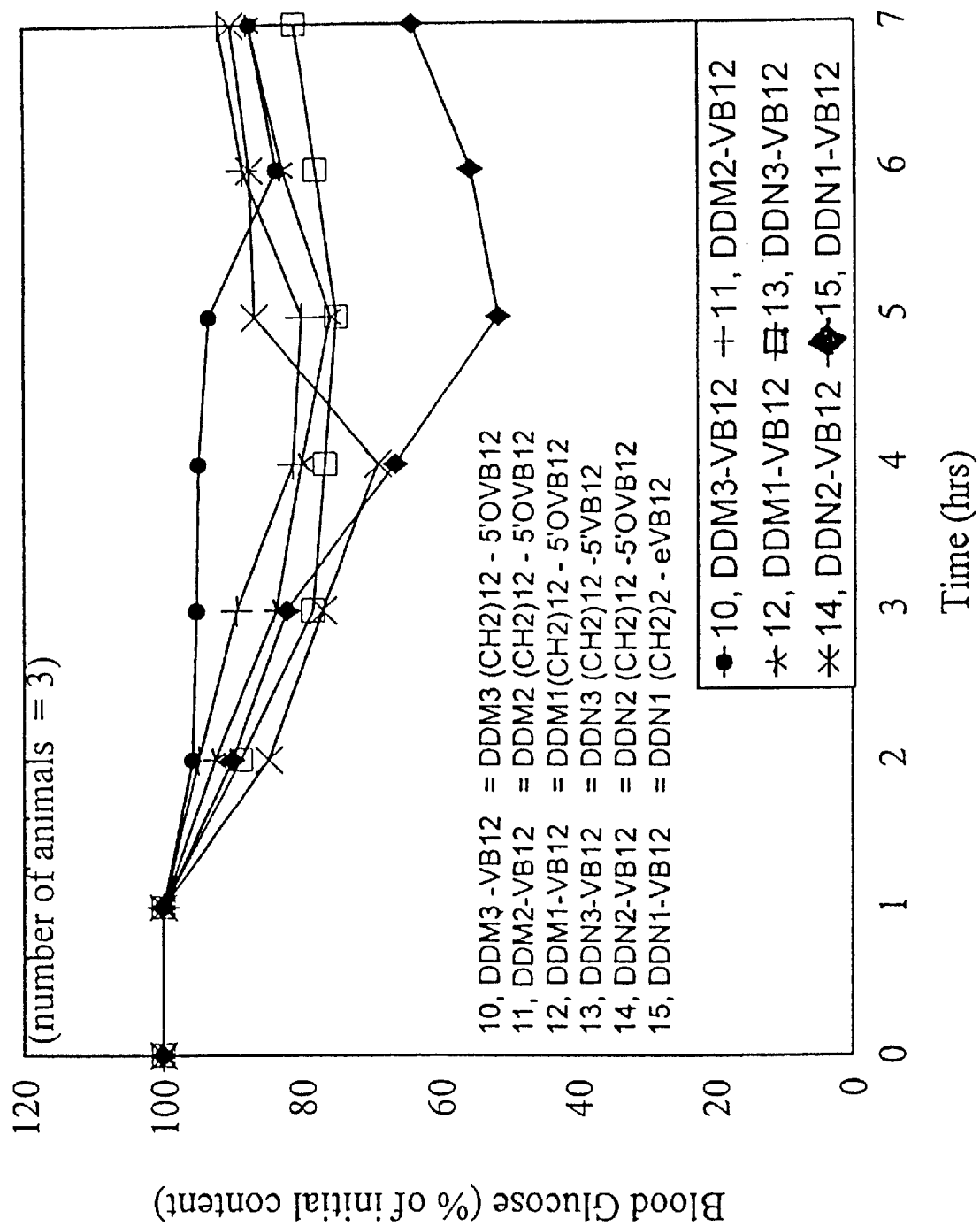
FIG. 4 graphical representation which shows hypoglycemic effect of oral administration of insulin loaded $VB_{12}$-sphere conjugates in streptozotocine induced diabetic rats.
Figure 5:
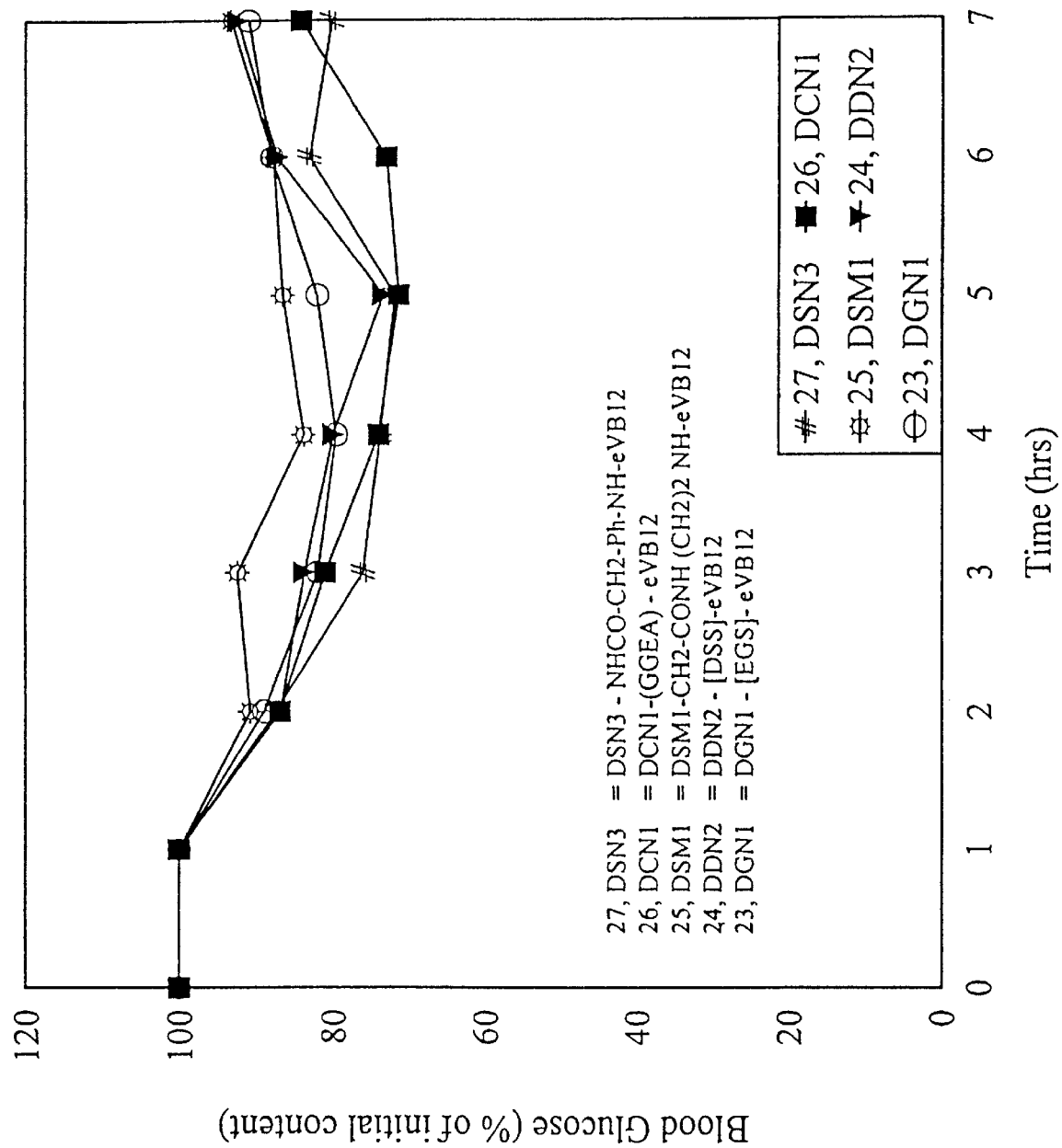
FIG. 5 graphical representation which shows hypoglycemic effect of oral administration of insulin-loaded $VB_{12}$ coated microsphere/nanoparticle conjugates in streptozoticin induced diabetic rats (n=3).
Figure 6:
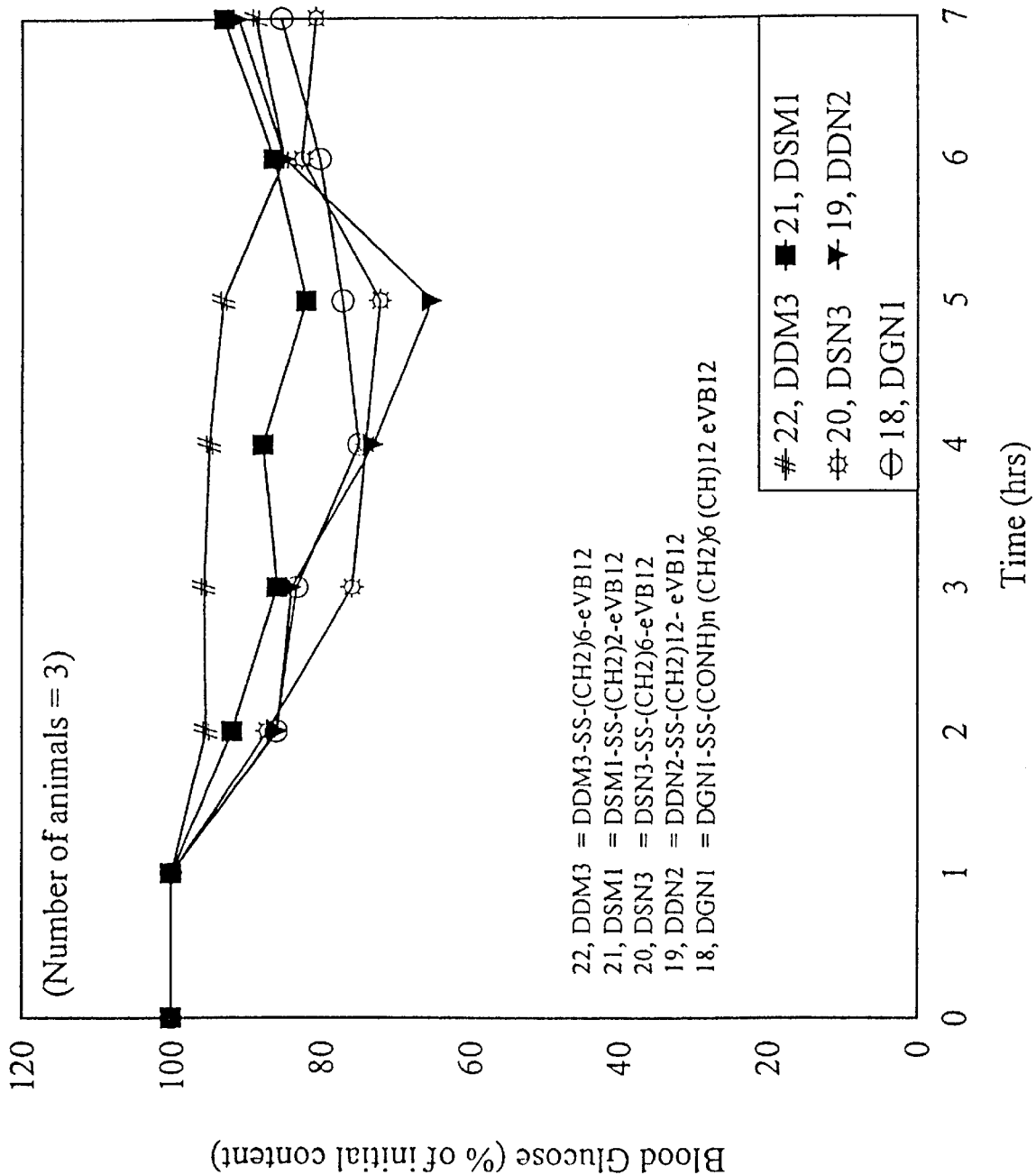
FIG. 6 graphical representation which shows hypoglycemic effect of oral administration of insulin-loaded $VB_{12}$ coated microsphere/nanoparticle conjugates in streptozoticin induced diabetic rats (n=3).
Figure 7:
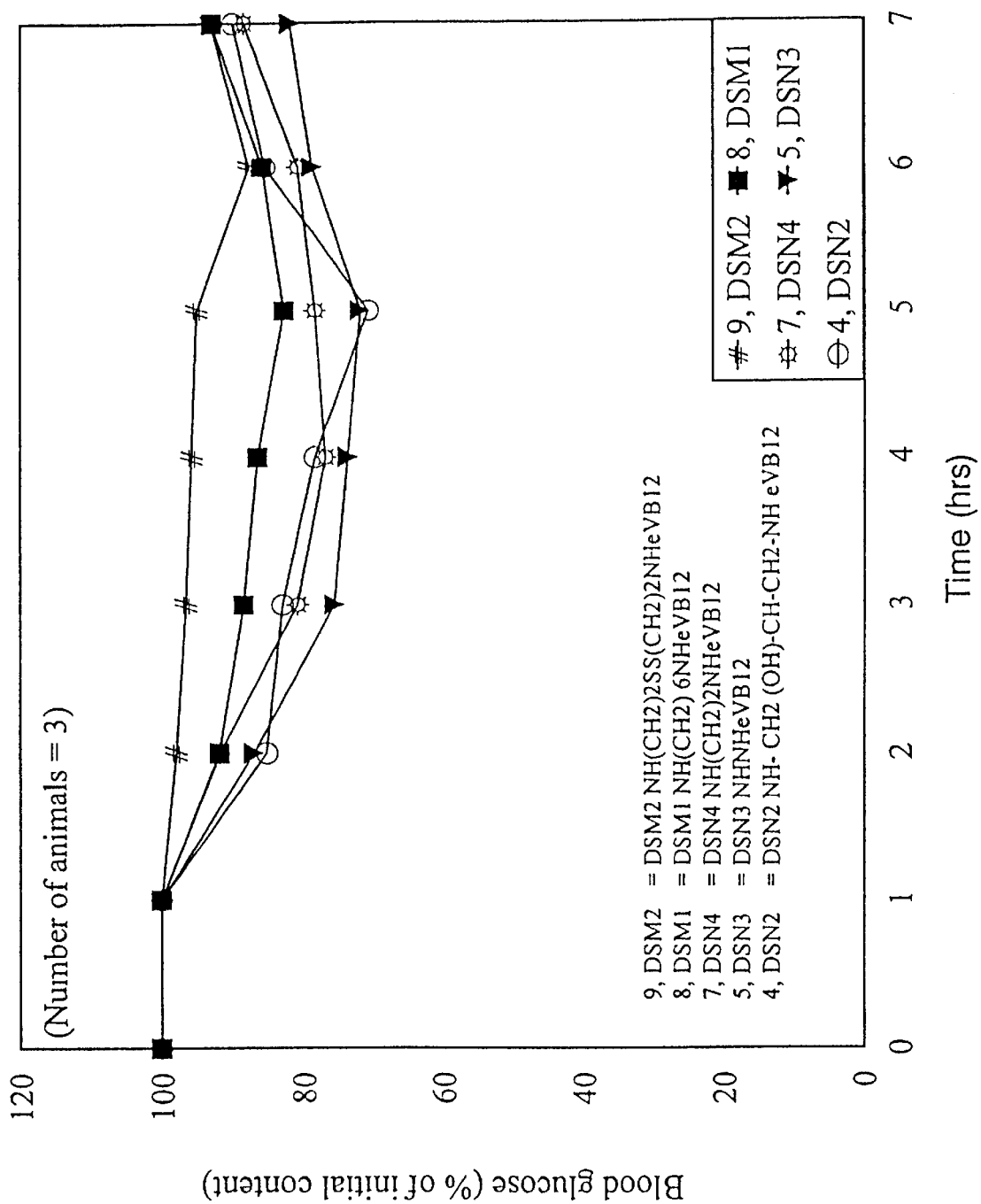
FIG. 7 graphical representation which shows hypoglycemic effect of oral administration of insulin-loaded $VB_{12}$ coated microsphere/nanoparticle conjugates in streptozoticin induced diabetic rats (n=3).
Figure 8:
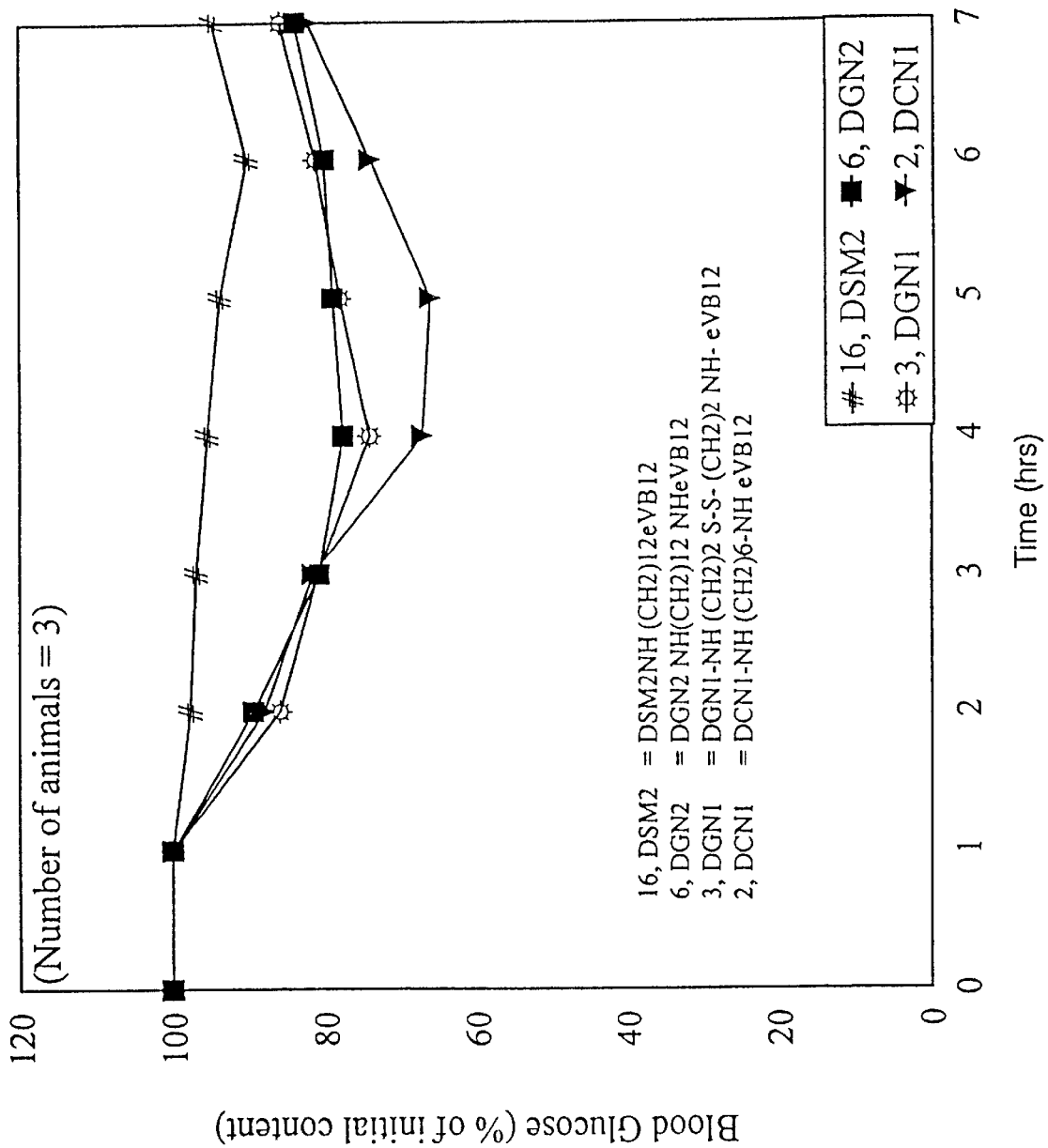
FIG. 8 graphical representation which shows hypoglycemic effect of oral administration of insulin-loaded $VB_{12}$ coated microsphere conjugates in streptozoticin induced diabetic rats (n=3).
Figure 9:
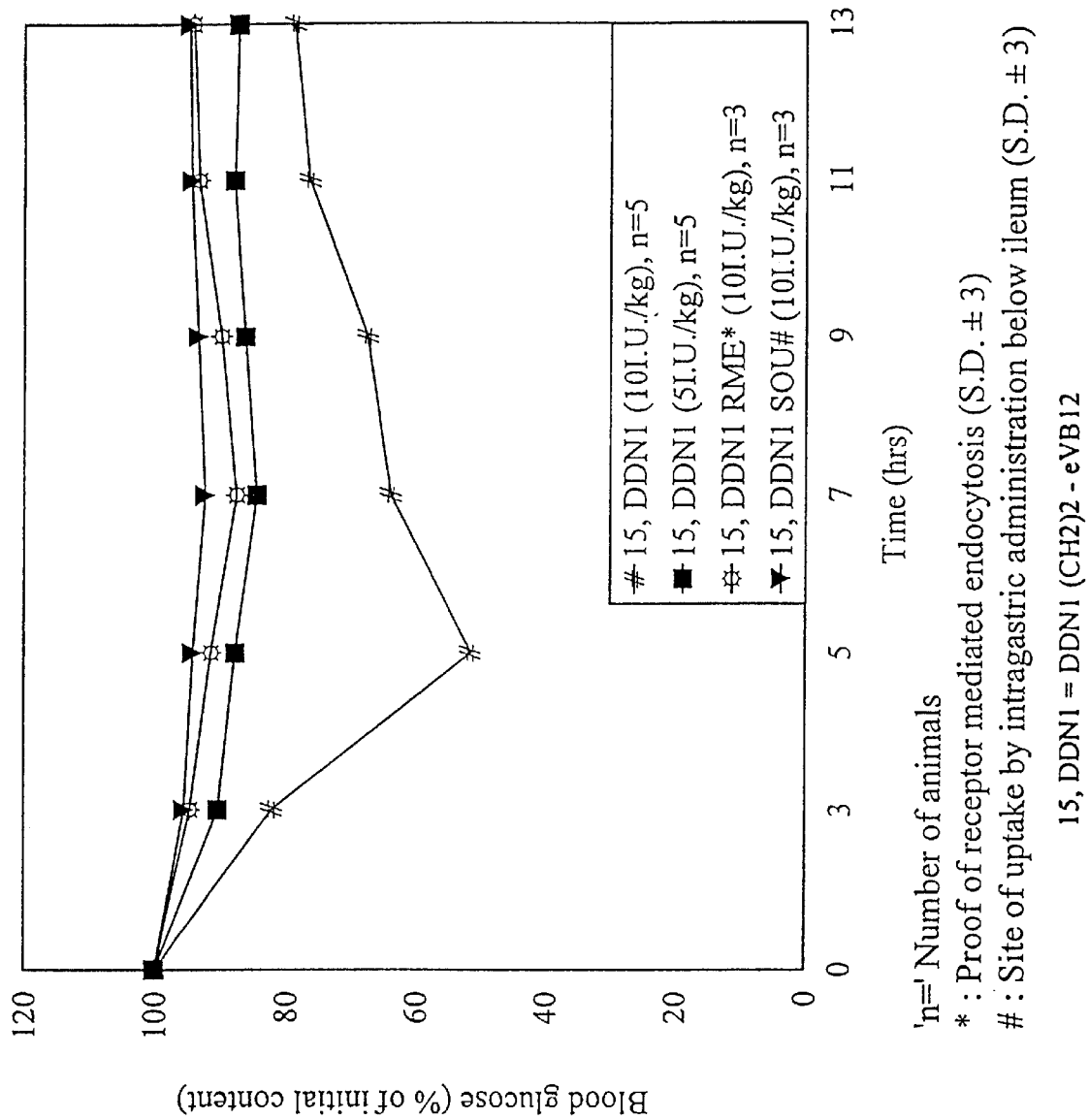
FIG. 9 graphical representation which shows dose response relation of effective delivery system (DDN1 CO—NH 'e' $VB_{12}$) and its uptake studies.
Figure 10:
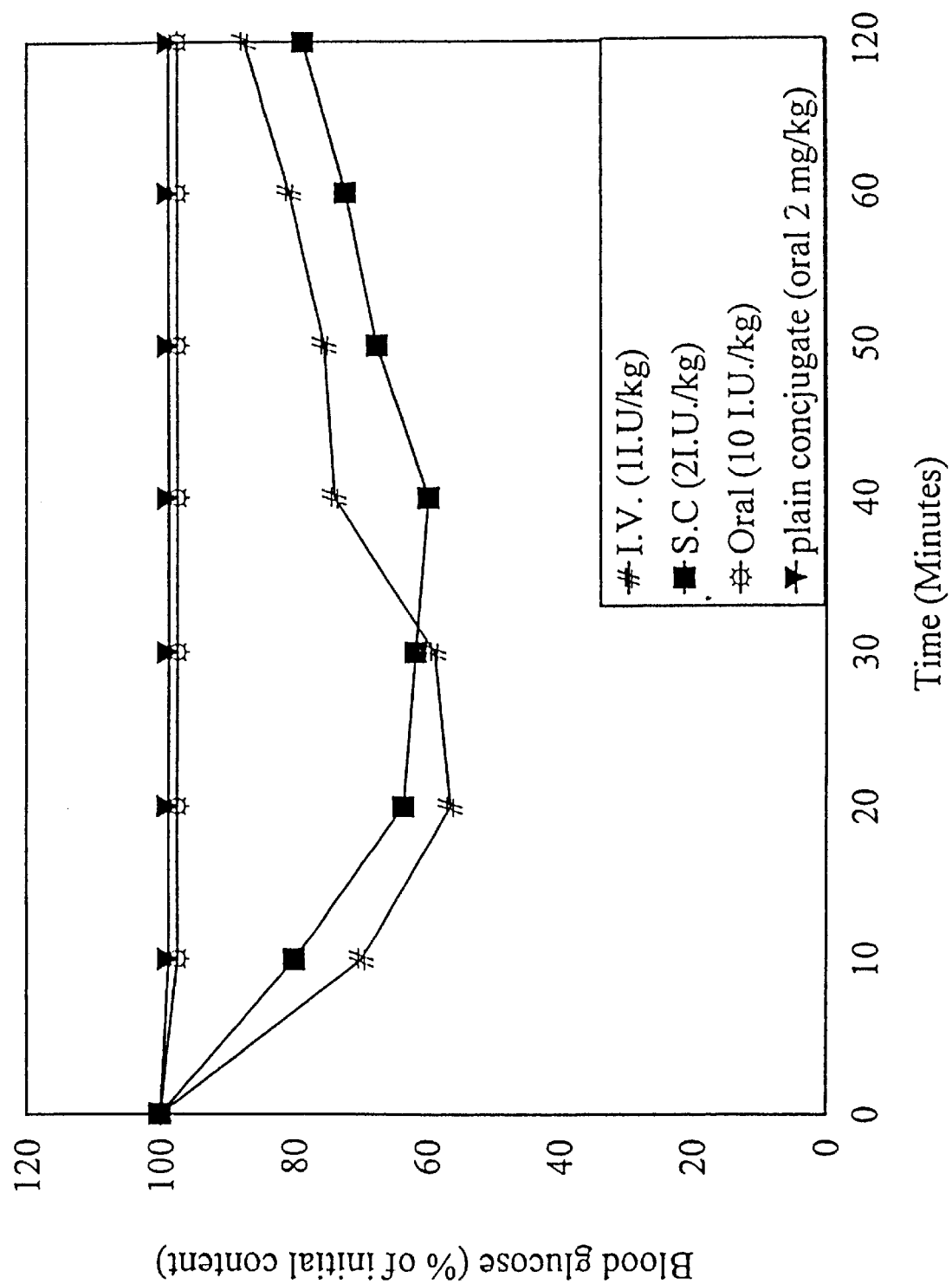
FIG. 10 graphical representation which shows hypoglycemic effect of plain conjugate and insulin given by I.V., S.C. and oral routes in streptozotocine induced diabetic rats.
Figures 11A, 11B:
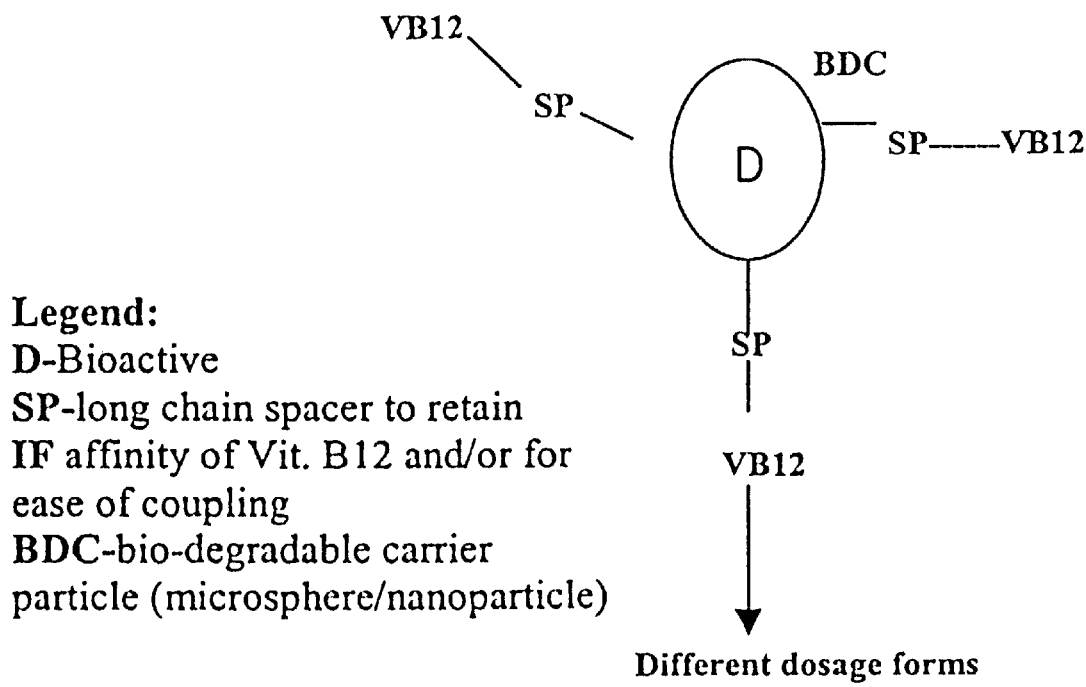
FIG. 11 shows schematic representation of present invention in comparison with earlier inventions.

Various $VB_{12}$ sphere conjugates were prepared as follows. The following are given by the way of illustration of the present invention and therefore should not be construed to limit the scope of the invention.

SECTION I 1.0 Synthesis of $VB_{12}$ Analogues Suitable for Conjugation

Native $VB_{12}$ (FIG. 2, 1a) was subjected to mild acid hydrolysis (0.4, M, HCl; 72h, RT) to produce a monoacid derivative from one of the three propionamide side chains (b, d and e) of the corrin ring. The 'e' monocarboxylate of $VB_{12}$ (1b), which has the highest affinity for IF (Kolhouse and Allen, 1977) was separated from b and d isomeric mixture by a combination of DOWEX AG 1×2 (Biorad) chromatography and semi-preparative $C_{18}$-RP-HPLC (with a gradient of 5–100% acetonitrile in 0.1% trifluoroacetic acid) (Anton et al., 1980).

1.1 Synthesis of Amino Derivatives of 'e' $VB_{12}$ (Russell Jones et al., 1995)

Amino derivatives of 'e' $VB_{12}$ were prepared by reacting the 'e' isomer of $VB_{12}$ (1b) with various spacers such as 1,2 diaminoethane, 1,6-diaminohexane, 1,12 diaminododecane, 1,3-diamino-2-hydroxypropane, and 1,6-diamino-3,4-dithiahexane (a.k.a cystamine) to produce amino 'e' $VB_{12}$ derivatives of 1c, 1d, 1e, 1f and 1g respectively. These reactions were carried out at pH 6.5 using 20 fold molar excess of diamine and 1-ethyl-3-[3-(dimethyl amino)propyl] carbodiimide (EDAC) respectively.

In a separate reaction 1,12 diaminododecane was coupled to native $VB_{12}$ (1a) to produce amino-dodecyl-5'O-$VB_{12}$ (1h) following activation of $VB_{12}$ with 1,1'-carbonyl diimidazole in dry DMF containing diisopropyl ethyl amine. Other amine derivatives can also be prepared at this site (data not shown).

All amino derivatives of $VB_{12}$ were purified by RP-HPLC (semi-preparative C4 column) with a gradient of 5–100% acetonitrile in 0.1% TFA. Eluted material was further purified by adsorption to S-Sepharose and elution with 0.1 M HCl. The amino derivatives were further purified by extraction into phenol and back extraction into water after the addition of methylene chloride to the phenol phase. Finally each of the products was lyophilized and recovered as a red-powder.

1.2 Synthesis of Dithiopyridyl (DTP) Amino $VB_{12}$ Derivatives

Three dithiopyridyl (DTP) amino-$eVB_{12}$ derivatives were prepared by reacting succinimidyl 3-(2-pyridyldithio) propionate (SPDP) with 2-aminoethyl-$eVB_{12}$ (1c) 6-aminohexyl-$eVB_{12}$ (1d) and 12-aminododecyl-5'O $VB_{12}$ (1h) to give the respective derivatives of (1i), (1j) and (1k). Typically the reaction was carried out by dissolving the amino-$VB_{12}$ derivative (50 mg/ml) in 0.1 M PO4 buffer, pH 7.5 containing 0.1 M NaCl, followed by the addition of 800 µl of solution of SPDP (50 mg/ml in acetone) to the amino-$eVB_{12}$ derivative. After overnight reaction at room temperature the DTP-amino-$eVB_{12}$ product was purified by RP-HPLC on a semi-preparative C4 column and then lyophilized.

1.3 Synthesis of Long Chain Dithiopyridyl (DTP) Amino-$VB_{12}$ Derivatives

These derivatives were prepared from the 6-aminohexyl-$eVB_{12}$ (1d) by sequential reaction with disuccinimidyl suberate (DSS) (to. give [[(monosuccinimidyl)suberyl]hexyl]-$eVB_{12}$) and 1,12-diaminododecane to give [[(12-aminododecyl)suberyl]hexyl]-$eVB_{12}$ (1 l). This product obtained was derivatized at the terminal amino group with SPDP, purified on RP-HPLC, and lyophilized to give derivative (1 m).

1.4 Synthesis of Hydrazidyl Derivatives of $e$-$VBz_{12}$ Carboxylate

These derivatives were prepared to couple to COOH particulates. Hydrazido-$e$ $VB_{12}$ (1 n) was prepared by a two-step synthesis involving the coupling of tertiary-butyl carbazate to $eVB_{12}$ carboxylate and subsequent removal of the t-Boc group to generate the free hydrazide. Cys-hydrazido-$eVB_{12}$ was synthesized from $eVB_{12}$ cystamine (1 g). The conversion of this material to $eVB_{12}$ Cys-hydrazide (1 o) proceeded by succinylation of the e $VB_{12}$ cystamine and subsequent conversion of the resultant terminal carboxyl group to a hydrazide by the procedure outlined above for $eVB_{12}$ hydrazide. The (adipylhydrazido)-$eVB_{12}$ reagent (1 p) was readily prepared in one step from $eVB_{12}$ carboxylate and a 20-fold excess of adipylhydrazide by the addition of EDAC.

1.5 Anilido Derivative of $eVB_{12}$ $eVB_{12}$ carboxylate (1b) was activated with NHS and EDAC and than coupled to para-aminopheyl acetic acid to give the $VB_{12}$ anilide (1q).

1.6 Formation of $VB_{12}$ Derivatives Containing Hindered Thiol Groups

Amino ethyl $eVB_{12}$ (1c) was coupled with 4-[(succinimidyl oxy)-carbonyl]- -methyl- -(2 pyridyldithio) toluene using standard literature conditions (Blackey et al., 1987).

The product -methyl- -(2 pyridyldithio)tolyl]-hexyl] $e$-$VB_{12}$ (1r) was purified by RP-HPLC.

1.7 Formation of Iodoacetamido Derivative of $VB_{12}$

Amino ethyl $eVB_{12}$ was converted to iodoacetamido derivative by reaction with NHS ester of iodoacetic acid. The product (1s) was purified by RP-HPLC.

1.8 Formation of Tetra Peptide Spacer Derivative of $eVB_{12}$ $eVB_{12}$ carboxylate (1b) was activated with EDAC and NHS, as previously described, was added to solution of tetrapeptide GGEA-OMe in bicarbonate buffer, pH 9.5. The product $VB_{12}$-GGEA-OMe (1t) was purified by RP-HPLC.

Structure of $VB_{12}$ and sites of linkage for IF affinity as shown in FIG. 2, wherein, 1a R'=NH$_2$; R"=H
1b R'=OH; R"=H
1c R'=NH(CH$_2$)$_2$NH$_2$: R"=H
1d R'=NH(CH$_2$)$_6$NH$_2$: R"=H
1e R'=NH(CH$_2$)$_{12}$NH$_2$: R"=H
1f R'=NHCH$_2$CH(OH)CH$_2$NH$_2$: R"=H
1g R'=NH(CH$_2$)$_2$SS(CH$_2$)$_2$NH$_2$: R"=H
1h R'=NH$_2$: R"=NH(CH$_2$)$_{12}$NH$_2$
1I R'=NH(CH$_2$)$_2$NHCO(CH$_2$)$_2$SS-Py: R"=H
1j R'=NH(CH$_2$)$_6$NHCO(CH$_2$)$_2$SS-PY: R"=H
1k R'=H: R"=NH(CH$_2$)$_{12}$NHCO(CH$_2$)$_2$SS-Py
1l R'=NH(CH$_2$)$_6$NHCO(CH$_2$)$_6$CONH(CH$_2$)$_{12}$NH$_2$: R"=H
1m R'=NH(CH$_2$)$_6$NHCO(CH$_2$)$_6$CONH(CH$_2$)$_{12}$NHCO(CH$_2$) SSPY:R"=H
1n R'=NHNH$_2$: R"=H
1o R'=NH(CH$_2$)$_2$SS(CH$_2$)$_2$NHCO(CH$_2$)$_2$NHNH$_2$: R"=H
1p R'=NHNHCO(CH$_2$)$_4$CONHNH$_2$: R"=H
1q R'=NH(CH$_2$)$_2$NHCOphCH$_2$COOH: R"=H
1r R'=NH(CH$_2$)$_2$NHCOphCH(CH$_3$)Sspy: R"=H
1s R'=NH(CH$_2$)$_2$NHCOCH$_2$I: R"=H
1t R'=NH-Gly-Gly-Glu-Ala-Ome: R"=H

SECTION II

Particulate carriers for drug loading are prepared by using natural, semi-synthetic and synthetic polymers of biodegradable nature. The polymeric particulate carriers prepared by various techniques are elaborated in this section.

2.0 Preparation of Cross-linked Polysaccharide Cores

Polysaccharide (PC) microparticles/nanoparticles of starch (DSM/DSN) and dextran (DDM/DDN were prepared by both emulsion and gel methodologies.
2.1.1 Preparation of PC Cores by Sonication of the Cross-linked Polymer Gel:

PC polymer cores were prepared according to the method of Samain et al (1989) with some modifications. 2 gm of polymer starch (Potato, soluble)/dextran (Mol. wt. 66,000 and 10,000) was dispersed (hydrolyzed) homogeneously in 1 M NaOH by vigorous shaking. Epichlorohydrin (0.18–0.4 ml) was then added under constant stirring for cross-linking. Shaking was stopped and the reaction was left to proceed at 70–80° C. until (usually 2–6 hrs) until a soft gel (white to pale yellow) was obtained. The resulting gel was diluted with water, mechanically ground and subjected to sonication with a probe sonicator (M/s Branson ultrasonified). The particulates so obtained were fractioned into different sizes by centrifugation and the precipitate (aggregates and larger particulates) was discarded. Finally, the chosen fractions were dried by lyophilization (DDM1, DDM2 and DDM3) or spray dried (DSM1 and DSM2) [mini spray dryer: Inlet temperature 200° C., out let temperature 140° C.; pump control 3, aspirator control 19, heating control 12, flow indicator 700] to get fine powder particulates.
2.1.2 Cross-linking Hydrolyzed Starch with POCl$_3$:

This was carried out according to method of Ignacio De Miguel et al., 1995 with some modifications. In this procedure, 5 gm of soluble starch (potato) was solubilized by homogenization in 2 M NaOH (10–12 ml). The temperature was adjusted to 4° C. by immersing in an ice bath then POCl$_3$ (2.5 gm 0.33 M) was added drop-wise together with a solution of 7.5 ml of 10 M NaoH under stirring. After addition of cross-linking agent it was further stirred at level 3 for 15 minutes (homogenizer). Then pH of the preparation was adjusted 7 with dil HCl. The resulting gel was diluted with water and subjected to sonication, centrifugation followed by spray drying (conditions same as above) to get fine powder (DSN1 and DSN2).

2.2 Interfacial Cross-linking by Emulsion Method
2.2.1 Cross-linking with Epichlorohydrin:

Some of the PC cores prepared by the above method showed some irregularities in shape, and so fresh microparticles were prepared by an emulsion method. Typically polysaccharide (2 gm Dextran mol. wt. 10,000 or soluble starch 5 gm) was solubilized in 1 M NaOH (5–10 ml). The polymer aqueous phase was emulsified in liquid paraffin (20–30 ml) containing span 80 (2%) by stirring at 15,000–22,000 rpm for 10 to 15 minutes to disperse the polymer droplets to a fine state. Then epichlorohydrin (0.5–1.0 ml) was added under agitation at 1000–5000 rpm with constant stirring at 70–80° C. for 2–3 hrs followed by addition of water (2–5 ml) and stirred for further 2–3 hrs with intermittent addition of water. The stirring was stopped until the white emulsion turned pale yellow with visible separation of colloidal particulate system (when agitation is stopped). The resultant particles were washed thrice with equal volume of petroleum ether/hexane and sufficient water. The organic phase was separated to remove oil phase from the aqueous particulate system. The aqueous particulate system was freeze dried/spray dried as described previously to get DDN1/DDN2 and DDN3/DSN3.
2.2.2 Cross-linking with POCl$_3$ by Emulsion Method:

5 gm of starch (potato soluble) was solubilized in 2 M NaOH (12.5 ml) and emulsified in liquid paraffin (40 ml) containing 2% span 80 by stirring at 22,000 rpm for 15 minutes. The temperature of dispersed aqueous polymer was brought to 4° C. (ice bath immersion), and cross-linking was carried out by adding POCl$_3$ (0.66 M 2.5 gm) drop wise together with a solution of 10 M NaOH (7.5 ml). This step was carried out under stirring at low rpm. The oil phase removed by washing three times with equal volumes of hexane/petroleum ether (separating funnel). The aqueous phase was diluted sufficiently, pH to 7.0 and finally spray dried as above to get fine powder DSN4.

2.3 Preparation of Cross-linked Guar Gum (GG) and Chitosan Hydrogels: (Kabir et al., 1998)

5 gm of chitosan solubilized in 0.5 M acetic acid solution (300 ml). Similarly 4 gm of guar gum was dispersed for 2 hrs at 45° C. in 800 ml water. Cross-linking was carried out by addition of 25% w/v glutaraldehyde. The reaction mixtures were homogenized for 30 at 22,000 rpm by the addition of 0.5 M concentrated H$_2$SO$_4$ followed by 25% w/v glutaraldehyde for chitosan emulsions and guar gum emulsions under the stirring at the same rpm. The reaction mixture was stirred for an additional 30 minutes at 15,000 rpm and kept in sealed container (separating funnel) for 48 hrs. The oil phase was removed by washing repeatedly with equal volumes of hexane. The aqueous phases were mixed with 5% w/v NaHCO$_3$ by stirring for 3–4 hrs and then rinsed with 1 liter of water until no traces of aldehyde were found. Then the particulate systems were spray dried to get chitosan products (DCN1 and DCN2) and guar gum products (DGM1 and DGM2) respectively.

2.4 Preparation of Nanoparticles by Solvent Evaporation Method

Procedure of Ando et al., 1999 (with some modification)
Microspheres and nanoparticles of poly (methylmethacrylate) (PMAM/PMAN), poly (hydroxybutyrate) (PHBM/PHBN), poly (D,L lactide)

(PLAM/PLAN) and poly (DL lactide Co-glycolic acid) (85:15) of different ratios (PLGAM/PLGAN) were prepared by water-oil-water double emulsion solvent evaporation process.

Due to the fragility of the protein bioactives encapsulation was carried out through cryopreparation (cold temperature) and carbohydrate (lyophilization and osmotic balance—in emulsion). The typical procedure is out-lined for the PLGA polymer. 500 μl (500 μg) of hepatitis 'B' surface antigen or 100–200 μl 100 IU insulin containing 80–100 mM trehalose was emulsified in 9–10 ml dichloromethane containing 100 mg PLGA by sonication for 10 seconds at 4–60° C. The primary emulsion temperature was than lowered below the freezing point of inner aqueous phase (dry ice/acetone) and then emulsified with 50–60 ml of 5% PVA (88% hydrolyzed) solution containing 100 mM trehalose (4–70° C.) at 6000–9000 rpm for 30–50 sec. The resulting secondary emulsion was diluted in 100 ml of 1% PVA and the system was stirred magnetically for 6–9 hrs to allow for evaporation of organic phase. The colloidal particles were finally collected by centrifugation and washing thrice with water to remove excess of PVA as well as protein bioactive. Particle size was controlled by changing level of sonication/agitation and also by centrifugation step to yield microspheres and nanoparticles and finally dried by lyophilization.

2.5 Preparation of Albumin Microspheres 2.5.1 Terephthaloyl Chloride Cross-linking:

3–4 ml solutions of (20–25% w/v) human serum albumin (HSA) in carbonate buffer (pH 9.8) were emulsified separately in chloroform:cyclohexane (1:4 w v/v) mixtures (15 ml) containing 4–5% v/v sorbitan trioleate. Then 20–35% solutions of terephthaloyl chloride were added (0.5, 1, 1.25 and 2.5% w/v) respectively. After 5–30 minutes of reaction time, the microspheres were washed, centrifuged, resuspended in PBS 7.4 and finally freeze-dried. Microspheres made in the conditions 1) pH 9.8, TC 2.5%, time 5 min and 2) pH 9.0, TC 2.5% and time 30 minutes were taken for conjugation.

2.5.2 Glutaraldehyde Cross-linking Using an Emulsion Method:

0.5 ml of 100 mg HSA was homogenized in 100 ml of cottonseed oil by slowly adding aqueous polymer phase drop wise to get w/o emulsion. 0.1 ml of an aqueous solution of glutaraldehyde (25% w/v) was added to the stabilized emulsion and stirring was continued for 1 hr, then 50 ml of acetone was added. After 1 minute microspheres were collected by centrifugation, washed with water, quenched with 10% w/v glycine solution (to remove reactive aldehyde groups), centrifuged appropriately, washed with water and lyophilized. Two centrifugation fractions were chosen HSAM and HSAN.

2.6 Preparation of Gelatin Nanoparticles

These were prepared according to a modification of the procedure of Lig et al., 1997. 1 ml of aqueous gelatin solution 7% w/v was added to 90 ml of cotton seed oil at 40° C. This biphasic system was homogenized at a speed of 22,000 rpm for 7–9 minutes to form w/o emulsion. The emulsion was cooled to a temperature of 40° C. (gelling point of gelatin) by keeping in a refrigerator when the emulsion turned to a suspension with the formation of gelatin nanoparticles, the oil phase was washed with hexane/petroleum ether. The aqueous particulate phase was then lyophilized to get DGN1.

* Where ever cross-linking is involved, drug loading is carried out at different stages i.e. either after preparation of particulate cargo or after coupling of $VB_{12}$ derivative.

2.7 Preparation of Poly(anhydride) Nanoparticles:
Phage Inversion Nano-encapsulation (PIN) Method Poly(anhydride) WP were prepared according to the procedure of Mathiowitz et al (1997). Protein (100 IU/mg, insulin/HBsAg 500 μg/mg) to be encapsulated (0.5–1 ml containing appropriate quantities to be encapsulated) was sonicated with 2–4% w/v of dichloromethane containing anhydride polymers of poly fumaric acid and sebacic acid and poly (FA:SA, 20:80) and poly fumaric acid:polylactide-co-glycolic acid [poly (FA:PLGA)50:50] for 10–20 sec at 4–6° C. The resulting dispersion was then poured rapidly into an unstirred bath of non-solvent such as petroleum ether (polymer solvent-non solvent ratio 1:100) to get polymeric nanoparticles. Desired particle size can be tailored by changing initial polymer %, solvent—non-solvent ratio and selection of non-solvent. The optimized formulations chosen were poly[FA:SA] 80:20 ® AFSN and poly[FA:PLGA] 50:50 ® AFPLGAN.

2.8 Poly Glutaraldehyde Nanoparticles

Margel, et al., (1979) processes with some modifications. 10 N NaOH was added drop wise to solution of to aqueous glutaraldehyde (3–25%) solution 100 ml containing surfactants (Guar C13 (1% and poly ethylene oxide mol wt. 10,000 (s)/or Aerosol 604 (1%)) until alkaline pH was reached (7–14, preferably 9–11). The mixture was de-aerated with $N_2$ gas in a tightly closed container and agitated on a mechanical shaker for 24 hrs at ambient temperature. On hourly intervals for 4–6 hrs the pH was adjusted to 11. Finally the system was dialyzed extensively with water and centrifuged to get PGL spheres (nanoparticles), particles of varying sizes that can be tailored by varying the concentration of monomer, surfactant or pH.

Two preparations of various optimized conditions PGLN1 (200 um) (COOH) and PGLN2 (400 nm) (CHO) were taken for coupling.

SECTION III

3.0 Particulate Sphere Surface Derivitazation Suitable for $VB_{12}$ Coupling Different methods of surface activation of the particulate carriers (microspheres/nanospheres) are illustrated as follows:

3.1.1 Activation by Periodate Oxidation:

The particulate fractions used for periodate oxidation were DSM1, DSM2, DSN1, DSN2, DSN3, DSN4, DCN1, DGN1 and DGN2.

The weighed quantity (250–500 mg) of microparticles was suspended in distilled water (5–10 ml) and was agitated by magnetic stirrer. Then sodium periodate (equal weight to particles) was added and mixing was continued for 45–50 minutes in the dark. The oxidized particulate system was thoroughly washed either by dialysis or centrifugation and finally lyophilized.

3.1.2 Coupling of $VB_{12}$ With Oxidized Particles.

The oxidized particulate system (100–150 mg) was then reacted with amino $VB_{12}$ derivative (20–30 mg) for 18–24 hrs at 4° C. in the dark. The conjugate was reduced by sodium borohydride (4 mg) for 2 h at 4° C., dialyzed and finally lyophilized as a powdered conjugate.

The $VB_{12}$ derivatives and particulates used were:

(Schematic representation of the reaction as mentioned in the following table.) Conj. $VB_{12}$ derivative+ Particle→Conjugate–(Size) No.

| Conj No | VB12 derivative + Particle | Conjugate | Size |
|---|---|---|---|
| 1 | 1O DSN1 | DSN1-NH NH—(CH$_2$)$_2$CONH(CH$_2$)$_2$—S—S—(CH$_2$)$_2$—NH eVB$_{12}$ | 207 ± 11 nm |
| 2 | 1d DCN1 | DCN1-NH(CH$_2$)$_6$—NH eVB$_{12}$ | 243 ± 18 nm |
| 3 | 1g DGN1 | DGN1-NH(CH$_2$)$_2$S—S—(CH$_2$)$_2$NH- eVB$_{12}$ | 261 ± 6 nm |
| 4 | 1f DSN2 | DSN2 NH—CH$_2$(OH)—CH—CH$_2$—NH eVB$_{12}$ | 410 ± 23 nm |
| 5 | 1n DSM3 | DSN3 NHNHeVB$_{12}$ | 792 ± 38 nm |
| 6 | 1e DGN2 | DGN2 NH(CH$_2$)$_{12}$NHeVB$_{12}$ | 914 ± 47 nm |
| 7 | 1c DSN4 | DSN4 NH(CH$_2$)$_2$NHeVB$_{12}$ | 1.2 ± 0.05 μm |
| 8 | 1d DSM1 | DSM1 NH(CH$_2$)$_6$NHeVB$_{12}$ | 4.1 ± 0.3 μm |
| 9 | 1g DSM2 | DSM2 NH(CH$_2$)$_2$SS(CH$_2$)$_2$NHeVB$_{12}$ | 6.6 ± 0.7 μm |

3.2.1 Surface Derivatization of the Particulates to Provide COOH Groups Suitable for Coupling with VB$_{12}$.

Surface derivatization of spheres to provide a functional group for VB$_{12}$ linkage: Particulates were succinylated using the method reported by Peyrot et al, (1994) to provide a functional group for linkage to amino VB$_{12}$ derivatives. The polysaccharide cores were first completely dried and then dispersed in dichloromethane (100 mg/ml) containing 50 mg/ml triethylamine. Succinic anhydride (30% w/w was added and the reaction was carried out under anhydrous conditions at (35×20° C.) for 20 hrs. Finally the chosen fractions DDM3, DDM2, DSM1, DDN1, DDN2 and DDN3, were dialyzed against distilled water and lyophilized.

3.2.2 Coupling of Succinylated Particles with VB$_{12}$ Derivatives:

VB$_{12}$-sphere conjugates were prepared by a direct amide linkage of the succinylated cores (DDM/DDN) with aminoderivatives of VB$_{12}$. In general, coupling was carried out by dispersing succinylated dextran cores in 0.15M NaCl solution (pH 4.5) and mixing it thoroughly with NH$_2$-Spacer VB$_{12}$ and 1-ethyl-3[(dimethylamino)propyl]carbodoiimide (EDAC) in a total of 3 ml. The pH was then adjusted to 7.5 with NaHCO$_3$. The reaction mixture was stirred at 30±2° C. for 2 hours and incubated at 4° C. for 20 hours and finally freeze-dried as dark pink to red powders. Typically 100 mg of succinylated cores were coupled with molar excess of (with respect to COOH) equal quantities of amino VB$_{12}$ and EDAC.

3.2.3 Alternative Method for Formation of VB$_{12}$ Spheres Using Aminohexyl-5'OVB$_{12}$:

1. Succinylated dextran cores were dispersed in solution (pH 4.5) at 100 mg/ml and mixed thoroughly with an equal volume of 50 mg/ml N-hydroxysuccinimide (50 mg/ml in DMF).
2. 1-ethyl-3{-3(dimethylamino)propyl}carbodiimide (EDAC) (equal weight to spheres) was added at 100 mg/ml, and allowed to react for 15 minutes.
3. An equal weight of Aminohexyl-5'OVB$_{12}$, (to spheres) dissolved at 100 mg/ml in 0.025 M K2CO3 was added and the reaction mixture was stirred at RT for 20 hours and finally dialyzed extensively against, before being lyophilized.

3.3.1 CNBR Mediated Coupling:

2 gm of CNBR was dissolved in 25 ml of PBS, pH 11.5 in a fume cup board. Then CNBR solution was added to particulate suspension under vigorous agitation for 10–15 minutes. In the above reactions pH was maintained by addition of NaOH. Particulates were centrifuged and thoroughly washed with ice-cold distilled water and sodium bicarbonate.

3.3.2 Coupling 25 mg of amino VB$_{12}$ was added to CNBR activated particles (100 mg) suspended in 3 ml bicarbonate buffer pH 7.5 and mixed by rotation for 72 hours at 4° C. and finally washed by centrifugation and extensive dialysis against buffer.

| S. No. | VB$_{12}$ derivative | + Particle → Conjugate | (Size) |
|---|---|---|---|
| 16) | 1e | + DSM2 → DSM2NH (CH$_2$)12eVB$_{12}$ | (6.6 ± 0.7 μm) |

3.4.1 Derivitization of Polysaccharide Particulates to Provide Amino Groups:

One of the amino groups of the diamine (1,2 diamino ethane) was protected by adding slowly 50% v/v benzyl oxychloride/acetic anhydride and purified by dowex chromatography. The mono protected diamine was treated with periodate activated particles/succinylated particulates. The protective group on the NH$_2$ group was removed to produce amino group of the particles on the surface.

3.4.2 Surface Modification to Provide Thiol Groups:

The amino groups modified particulate system was dispersed in phosphate buffer, pH 7.5 (50 mg/ml). SPDP was dissolved in acetone (50 mg/ml). Both the phases were mixed thoroughly and left to proceed at room temperature over night and excess of the reagent removed by dialysis. A free thiol was introduced by reduction with β-mercaptoethanol and finally lyophilized.

| Conjugate No. | VB$_{12}$ derivative | + particle → Conjugate | (Size) |
|---|---|---|---|
| 10) | 1h | + DDM3 → DDM3 (CH$_2$)$_{12}$-5'OVB$_{12}$ | (6.1 ± 0.9 μm) |
| 11) | 1h | + DDM2 → DDM2 (CH$_2$)$_{12}$-5'OVB$_{12}$ | (3.6 ± 0.39 μm) |
| 12) | 1h | + DDM1 → DDM1 (CH$_2$)$_{12}$-5'OVB$_{12}$ | (1.7 ± 0.32 μm) |
| 13) | 1h | + DDN3 → DDN3 (CH$_2$)$_{12}$-5'VB1$_{12}$ | (875 ± 52 nm) |
| 14) | 1h | + DDN2 → DDN2 (CH$_2$)$_{12}$-5'OVB$_{12}$ | (436 ± 38 nm) |
| 15) | 1c | + DDN1 → DDN1 (CH$_2$)$_2$-eVB$_{12}$ | (164 ± 13 nm) |

3.4.3 Formation of VB$_{12}$-polysaccharide Conjugates by Disulfide Linkage:

SPDP treated particles (25 mg/ml; 50 mg/ml) were suspended in sodium acetate buffer, pH 4.5. Then 2.5 ml of DTP amino ethyl derivative (10 mg/ml) dissolved in acetate buffer, pH 4.5. Both phases were mixed and the reaction allowed to proceed for 48 hours at 40° C. The conjugates were dialyzed and finally lyophilized. The various derivatives used and their conjugates from the above reaction are given below:

| S.No. | VB$_{12}$ derivative | + Particle | → Conjugate | (Size) |
|---|---|---|---|---|
| 17) | 1K | + DCN1 | → DCN1-SS—(CH)$_{12}$eVB$_{12}$ | (243 ± 13 nm) |
| 18) | 1m | + DGN1 | → DGN1-SS—(CONH)n (CH$_2$)$_6$(CH)$_{12}$eVB$_{12}$ | (261 ± 16 nm) |
| 19) | 1r | + DDN2 | → DDN2-SS—(CH$_2$)$_{12}$-eVB$_{12}$ | (436 ± 38) |
| 20) | 1j | + DSN3 | → DSN3-SS—(CH$_2$)$_6$-eVB$_{12}$ | (792 ± 45 nm) |
| 21) | 1i | + DSM1 | → DSM1-SS—(CH$_2$)$_2$-eVB$_{12}$ | (4.1 ± 0.41 μm) |
| 22) | 1j | + DDM3 | → DDM3-SS—(CH$_2$)$_6$-eVB$_{12}$ | (6.1 ± 0.9 μm) |

3.5.0 Formation of Noncleavable VB$_{12}$-polysaccharide Core Conjugates:

1) Micro particles containing NH$_2$ groups (DGN1-previously modified with monoprotected diamine) on the surface were treated with 1.5 fold molar excess of ethylene glycol bis (succinimidyl succinate) [EGS] for 20 minute at room temperature. Amino eVB$_{12}$ (1c) was added and the coupling carried out over night. The product was dialyzed/centrifuged and lyophilized.

2) Similarly, a particulate system (DDN2-previously modified with mono-protected diamine) was treated with disuccinymidyl suberate (DSS). The reaction intermediate was treated with amino VB$_{12}$ (1d) and the conjugate washed and lyophilized.

3) To SPDP modified particles (DSM1), a solution of iodoacetemido hexyl eVB$_{12}$ (1s) in diisopropyl ethylamide/diethyl formamide (1:20 v/v) was added under vigorous stirring (at inert atmosphere) for 30 minutes at room temperature and the thioether conjugate was washed and lyophilized.

4) The tetrapeptide eVB$_{12}$ (1t) was conjugated to amino group containing particles ((DCN1-previously modified with mono-protected diamine, 3.4.1) in the presence of EDAC/NHS in bicarbonate buffer, pH 9.5 for 30 minutes at room temperature and was mixed with 2% acetic acid washed and lyophilized.

5) The anilido derivative of eVB$_{12}$ (1q) was coupled with amino group containing particles (DSN3-previously modified with mono-protected diamine, 3.4.1) in the presence of EDAC/NHS in bicarbonate buffer, pH 9.5 for 30 minutes at room temperature and diluted with 2% acetic acid, washed and lyophilized.

| S.No. | VB12 Derivative | + particle | → Conjugate | (Size) |
|---|---|---|---|---|
| 23. | 1C | + DGN1 | → DGN1-[EGS]-eVB$_{12}$ | (261 ± nm) (Activity less) |
| 24. | 1d | + DDN2 | → DDN2-[DSS]-eVB$_{12}$ | (436 ± 38 nm) |
| 25. | 1s | + DSM1 | → DSM1-CH2—CONH(CH2)2 NH-eVB$_{12}$ | (4.1 ± 0.41 μm) |
| 26. | 1t | + DCN1 | → DCN1-(GGEA)-eVB$_{12}$ | (243 ± 13 nm) |
| 27. | 1q | + DSN3 | → DSN3-NHCO—CH2—Ph—NH-eVB$_{12}$ | (792 ± 45 nm) |

3.6 Amide Conjugates of Amino VB$_{12}$/Hydrazide and Micro Particles Prepared by Solvent Evaporation by EDAC 20 fold molar excess of amino VB$_{12}$/hydrazide VB$_{12}$ and EDAC were used to couple to particles containing COOH in bicarbonate buffer, pH 7.5 and conjugation was carried out overnight at 4° C., washed and lyophilized. Particulates used and their $VB_{12}$ derivatives are given below:

| S.No. | $VB_{12}$ Derivative | + Particle | → conjugate | (Size) |
|---|---|---|---|---|
| 28) | 1p | + PLGAN1 | → PLGAN1 CONHNH-spa-e$VB_{12}$ | (120 ± 6.0 nm) |
| 29) | 1c | + PLGAN2 | → PLGAN2 CONH-e$VB_{12}$ | (135 ± 7.0 nm) |
| 30) | 1d | + PLGAM3 | → PLGAM3 CONH-spa-e$VB_{12}$ | (1.5 ± 0.09 μm) |
| 31) | 1o | + PHBN1 | → PHBN1 CONH—SS-spa-e$VB_{12}$ | (173 ± 6.0 nm) |
| 32) | 1n | + PHBN2 | → PHBN2 CONHNH-e$VB_{12}$ | (932 ± 30.0 nm) |
| 33) | 1e | + PLAN1 | → PLAN1 CONH-spa-e$VB_{12}$ | (190 ± 9.0 nm) |
| 34) | 1g | + PLAM2 | → PLAM2 CONH—SS-e$VB_{12}$ | (3.4 ± 0.3 μm) |

3.6.1 $VB_{12}$ Particulate Systems Coupled by Disulfide Linkages:

The nanoparticles PLGAN1, PLGAN2, PHBN1 and PLAN1 were surface modified with monoprotected diamine and treated with SPDP as described previously (section 3.2.1 and 3.2.2) to give SH containing particles.

3.6.2 Derivatization of Particulates to Provide Amino Groups:

One of the amino groups of the diamine (1,2 diaminoethane) was protected by adding slowly 50% v/v benzyl oxychloride/acetic anhydride and purified by DOWEX chromatography. The mono protected diamine was treated with particulate systems, and the protective group on the $NH_2$ group was removed to produce amino group of the particles on the surface.

3.6.3 Surface Modification to Provide Thiol Groups:

The amino groups modified particulate system was dispersed in phosphate buffer, pH 7.5 (50 mg/ml). SPDP was dissolved in acetone (50 mg/ml). Both the phases were mixed thoroughly and left to proceed at room temperature over night and excess of the reagent removed by dialysis. A free thiol was introduced by reduction with B-mercaptoethanol and finally lyophilized.

3.6.4 Coupling:

SPDP treated particles (25 mg/ml, 50 mg/ml) were suspended in sodium acetate buffer, pH4.5. Then 2.5 ml of DTP amino ethyl derivative (10 mg/ml) dissolved in acetate buffer, 4.5. Both phases were mixed and the reaction allowed to proceed for 48 hours at 4° C. The conjugates were dialyzed and finally lyophilized.

6.6.5 Co-incorporation of Surface Functional Groups for Linkage into Nanospheres (PLGA):

Surface functional groups suitable for $VB_{12}$ linkage are co-administered to the nano sphere matrix during preparation. Nanospheres containing (L-alpha-phosphatidyl ethanolamine) were prepared by mixing a chloroform solution of lipid to a polymer solution in dichloromethane (lipid to polymer ratio 1:5). Emulsification was then carried out as above (PLGA solvent evaporation process) PGLAN2. The formed particles were modified with SPDP to make them suitable for coupling.

These systems were designed for conjugation to dithiopyridyl derivate of $VB_{12}$.

| Cong. No. | $VB_{12}$ derivative | + Particle | → conjugate | (Size) |
|---|---|---|---|---|
| 35) | ij | + PLGAN1 | → PLAGN1-SS-e$VB_{12}$ | (120 ± 6.0 nm) |
| 36) | 1k | + PLGAN2 | → PLGAN2-SS-e$VB_{12}$ | (135 ± 7.0 nm) |
| 37) | 1m | + PHBN1 | → PHBN1-SS-e$VB_{12}$ | (170 ± 6.0 nm) |
| 38) | 1i | + PLAN1 | → PLAN1-SS-e$VB_{12}$ | (190 ± 9.0 nm) |

3.6.6 Adsorption of $VB_{12}$ Derivative Copolymers on Colloidal Particulates:

This was done by the method of Neal et al., with some modifications by $VB_{12}$ coupling on poloxamers Neal et al., 1998.

Step 1:

The terminal hydroxyl groups in poloxamer 407 and poloxamine-908 were substituted with amino groups followed by coupling of the amino copolymers with $VB_{12}$.

1) e-carboxylate of $VB_{12}$ (1b) in presence of EDAC as above. The reactions were slightly modified to include an organic solvent, tetrahydrofuran instead of aqueous solvents as used previously.

2) In another reactions the amino copolymers were modified with SPDP, followed by linkage with dithiopyridyl derivatives of e$VB_{12}$ (1i) as described previously.

The procedure for amino derivatization of copolymers is out-lined briefly (Ref. Neal, J. C. et al., 1998). 20% w/v solution of copolymer in $CH_2C_{12}$ was reacted with a 2-fold molar excess of p-toluenesulfonyl chloride and pyridine at room temperature for 24 h. The p-toluenesulfonate ester product was extracted by first washing with 3 M HCl, followed by washing the organic layer with $NaHCO_3$, with rotary evaporation used to obtain the copolymer. In the second step, the p-toluenesulfonate ester product was reacted with 25% w/v NH3 in $H_2O$ for 6 h at 120° C. in a pressurized reaction vessel, to produce the aminated copolymer. The reaction products were cooled to room temperature and extracted with $CH_2C_{12}$ to separate the ammonium toluenesulfonate salt from the aminated copolymer. The product was then washed with base ($NaOH/H_2O$) to produce the free amino product.

Step 2:

The aminated copolymers of $VB_{12}$ were adsorbed onto nanoparticle surface. Briefly $VB_{12}$ derivatized copolymer 0.5% w/v solutions were incubated for 12 hr with equal volume and concentration of microparticle suspension.

Conjugates Adsorbed on Nanoparticles

| Cong. No. | eVB$_{12}$ derivative | + particle | → | Conjugate | (Size) |
|---|---|---|---|---|---|
| 39) | P-407NHCO-eVB$_{12}$ (eVB$_{12}$-polo-eVB$_{12}$) | + PLGAN1 | → | PLGAN1-P407-eVB$_{12}$ | (120 ± 6.0 nm). |
| 40) | P-908NHCOeVB$_{12}$ | + PGBN1 | → | PHBN1-P908-eVB$_{12}$ | (173 ± 6.0 nm) |

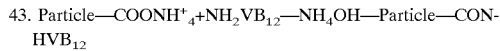

| | | | | | |
|---|---|---|---|---|---|
| 41) | P407-SS-eVB$_{12}$ | + PHBN1 | → | PHBN1-P407-SS-eVB$_{12}$ | (173 ± 6.0 nm) |
| 42) | P-908-SS-eVB$_{12}$ | + PLGAN1 | → | PLGAN1-P908-SS-eVB$_{12}$ | (120 ± 6.0) |

Surface Adsorption

Particulate systems containing surfacial COOH groups are anionic in nature, mixing them with cationic agents gives their adsorption by ionic bond on the nanoparticle surface. The required quantity of the surface-modifying agent can be adsorbed. Typically for particles with 5–10% DMAD, 5–10 mg of this agent dissolved in 10–20 ml water containing 95–90 mg of preformed particles, was suspended by sonication on an ice bath and dried by lyophilization.

43. Particle—COONH$^+_4$+NH$_2$VB$_{12}$—NH$_4$OH—Particle—CONHVB$_{12}$

Epoxy Activation of Nanoparticles: Vinod et al., 1998

A sample of (80) of pre-formed nanoparticles was suspended in 10 ml of borate buffer (50 MM, pH5) over in an ice bath. Then, zinc tetrafluroborate hydrate (catalyst 24 mg) and Denacol solution (24 mg in 4-ml borate buffer) were added while stirring at 37±1° C. for 30–50 minutes. The nanoparticles were separated by centrifugation and washed extensively with H$_2$O to remove unreacted impurities.

44. Particle COOH+DeOH—Particle COO—De—OH

Amino derivatives VB$_{12}$ are coupled by 1,1'carbonyl diimidazole activation.

3.6.7 Conjugation of Anhydride Particles Prepared by PIN Method:

Weighed quantities of polyanhydride nanoparticles [ASSN1, AFPLGAN2; 50 mg each] were suspended in borate buffer [0.20 M, pH 9.0, 10ml] then a hydrazide derivative of eVB$_{12}$ was added in molar excess over anhydride groups of nanoparticles. After 30 minutes acetate buffer [0.2 M, pH 5.0, 25 ml] was added. The conjugated nanoparticles were washed with 2 M NaCl, distilled water and lyophilized.

| Cong. No. | eVB$_{12}$ derivative | + particle | → Conjugate | (Size) |
|---|---|---|---|---|
| 45) | 1o | + AFSN1 | → AFSN1-CONHNH—SP-eVB$_{12}$ | (500 ± 22 nm) |
| 46) | 1p | + AFPLGAN1 | → AFPLGAN1CONHNH—SP-eVB$_{12}$ | (200 ± 9.0 nm) |

3.6.8 Disulfide Conjugates of Anhydride Particles and eVB$_{12}$:

The particles (AFSN1, AFPLGAN2) were surface modified with mono-protected diamine and the protecting agent cleaved as described previously (Section 3.6.2).

In another reaction nanoparticles (AFSN1) were surfaced modified with arginamide Ref. (Gao, J. et al., 1998). Briefly 50 mg of nanoparticle were suspended in a solution containing 12 mM arginamide in borate buffer (0.20 M, pH 9.0, 3 ml at R.T.). After 15 minutes the suspension was acidified by adding acetate buffer (0.20 M, pH 5.0, 9 ml). The particles were washed with 2M NaCl, distilled water and lyophilized.

The above amino derivatized particles were coupled to SPDP to give particles containing SH groups as described previously (section 3.6.3).

The coupling is carried out as described in 3.6.4.

| Cong. No. | eVB$_{12}$ derivative | + particle | → Conjugate | (Size) |
|---|---|---|---|---|
| 47. | 1k | + AFSN1 (Amino → SH) | → AFSN1-SS-eVB$_{12}$ | (500 ± 22 nm) |
| 48. | 1j | + AFPLGAN2 (Amino- → SH) | → AFPLGAN2-SS-eVB$_{12}$ | (200 ± 22 nm) |
| 49. | 1i | + AFSN1 (Arginamide- → SH) | → AFSN1-SS-eVB$_{12}$ | (500 ± 22 nm) |

3.6.9 Conjugation of Protein Polymer Based Micro/Nanoparticles to VB$_{12}$:

Different fractions of microparticles and their conjugates are given below:

In this reaction HSAM particles (100 mg) were activated with 0.25–0.5 ml, 25%w/v glutaraldehyde in borate buffer that forms Schiff's base and gives CHO groups for conjugation. The disulfide coupling between particulates and VB$_{12}$ derivative is carried out as described in 3.6.2., 3.6.3 and 3.6.4.

2000 (vide infra) was dissolved in 0.25 mL of deionized water. To the solution was added 0.5 mL of a buffered solution with or without FITC-BSA (10 mg/mL) and 0.25 mL of 8-arm PEG-amine solution (250 mg/mL). After vigorous shaking, the solution was allowed to sit. The gel formed in a few minutes. A suitable pH range was 5.5 to 8.

A two-step gel made from difunctional PEG-succinimidyl carbonate containing an ester in the fifty milligrams of difunctional ester containing PEG-succinimidyl carbonate 6800 (vide infra) was dissolved in 0.3 mL of deionized

| Cong. No. | eVB$_{12}$ derivative | + particle | (Surface nature) | → Conjugate | (Size) |
|---|---|---|---|---|---|
| 50. | 1p | + HSAM1 | (anhydride & HOC) | → HSAM1-CONHNH-spa-eVB$_{12}$ | (3.7 ± 0.18 μm) |
| 51. | 1e | + HSAM2 | (anhydride & NH2) | → HSAM2-CONH—(CH)$_{12}$-eVB$_{12}$ EDAC reduction | (6.4 ± 0.3 μm) |
| 52. | 1k | + HSAM2 + SPDP | (SH groups) | → HSAM2-SS-spa-eVB$_{12}$ | (6.4 ± 0.3 μm) |
| 53. | 1o | + DAN1 | (COOH) | → EDAC DAN1-Co—NHNH-spa-eVB$_{12}$ | (534 ± 23 μm) |
| 54. | 1d | + DAM2 | | → COOH → DAM2CONH—(CH$_2$)$_6$-eVB$_{12}$ reduction | (2.3 ± 0.9 μm) |
| 55. | 1l | + DGN1 + SPDP | → SH | → DGN1-SS-eVB$_{12}$ | (700 ± 31 m) |
| 56. | 1b | + DGN2 | (NH2) | → DGN1-NHCO-eVB$_{12}$ | (914 ± 47 nm) |

3.7 Coupling of Poly Glutaraldehyde Nanoparticles to eVB$_{12}$

An aqueous particulate suspension (PGLN2, 100 mg/ml; 5 ml) was diluted with PBS (pH 7.4, 15 ml). Then hydrazide VB$_{12}$ derivative (10 ml, 15–20 mg) solution was added under stirring for 2 hrs at 4° C. then glycine (200 mg) was added to remove the reactive aldehyde groups and agitation was continued for another 1 hr at R.T. The particles were dialyzed/centrifuged and finally lyophilized. PGLN1 was coupled with amino hexyl eVB$_{12}$ (1d) by carbodiimide chemistry.

water. To the solution was added 0.3 mL of 8-arm PEG amine (250 mg/mL). After vigorous shaking, the solution was allowed to sit. The gel formed in a few minutes. A suitable pH range was 5.5–8.

Conjugates 59 and 60: Amino and hydrazide derivatives are coupled during the preparation.

SECTION IV

Protein Loading (Insulin) into the Preformed Conjugate

Typically 100 I.U. of plain bovine insulin solution (40 I.U./ml) or a solution of 500 μg hepatitis 'B' vaccine was

| Cong. No. | eVB$_{12}$ derivative | + particle | → Conjugate | (Size) |
|---|---|---|---|---|
| 57. | 1d | + PGLN1 | → PGLN1-CONH(CH$_2$)$_6$eVB$_{12}$ Reduction | (200 ± 12 nm) |
| 58. | 1o | + PGLN2 | → PGLN2-CH$_2$—NHNH-spa (SS)-eVB$_{12}$ | (400 ± 27 nm) |

3.8 Degradable Hydrogel by Covalent Coupling of VB$_{12}$ Derivatives

Ref: Zhao, X. and Harris, J. (1998)

Two step hydrogel preparation—A two-Step Gel made from difunctional double-Ester PEG-fifty milligrams of difunctional PEG-CM-HBA-N-hydroxysuccinimide (NHS)

mixed with preformed conjugates containing 100 mg of polysaccharide cores. The gel was freeze-dried and a dark pink to pale red powder and stored at 4–8° C. until use. Wherever, cross-linking is involved drug loading is carried out at different stages i.e. either after preparation of particulate cargo or after coupling of VB$_{12}$ derivative.

Specific Advantages

The delivery system described in this invention has advantages over the other reported $VB_{12}$ based conjugated systems (1) The pharmaceutical to be delivered is loaded in the biodegradable polymeric carriers. (2) Particulate carriers prepared in this invention are made up of biodegradable and pharmaceutically acceptable carriers and hence degrade in-vivo to release and deliver the bioactive for its pharmacological response, which is a prerequisite for drug delivery. (3) Peptide/protein pharmaceuticals or vaccines or drugs given exclusively by parental groups can easily be loaded within the biodegradable polymers for pharmaceutical purpose. (4) Polymeric particles afford protection against harsh environment of the intestine and gut enzymes. (5) Uptake is amplified many times as compared to $VB_{12}$ protein conjugated system. (6) The pharmaceutical to be delivered is not chemically modified and hence retains its fall bioactivity.

In-vivo Performance

Various insulin loaded drug delivery systems prepared were tested for antidiabetic activity in Streptozotocin induced diabetic rats and the results are briefed in summary section. These insulin drug delivery systems are orally administered to diabetic rats (n=number of animals). At various time intervals after feeding the rats were bled and their blood glucose levels determined.

What is claimed is:

1. A complex for oral delivery of drugs, therapeutic proteins and peptides, and vaccines, which are loaded in a Vitamin $B_{12}$ ($VB_{12}$) coupled particulate carrier system having one or more spacers in between, and having the formula $VB_{12}$—R'/R"—N, wherein each of R' and R" is a spacer for the derivative of said $VB_{12}$ to provide $NH_2$, COOH, or SH group; N is a micro or nano particle carrier for the delivery of injectable drugs, therapeutic proteins and peptides, and vaccines; and said $VB_{12}$ retains its intrinsic factor (IF) affinity after coupling to said carrier through said spacer.

2. A complex as claimed in claim 1, wherein said drugs, therapeutic proteins and peptides, and vaccines are selected from the group consisting of drugs, therapeutic proteins and peptides, and vaccines heretofore administered exclusively by parenteral routes.

3. A complex as claimed in claim 1, wherein said drug is gentamycin or amikacin.

4. A complex as claimed in claim 1, wherein said carrier system is a biodegradable polymeric particulate carrier.

5. A complex as claimed in claim 1, wherein said $VB_{12}$ is a native cyanocobalamin ($VB_{12}$) or its analog selected from the group consisting of:

aquocobalamin, adenosylcobalamin, methylcobalamin, hydroxycobalamin and their derivatives, alkylcobalamine in which alkyl chain is linked to cobalt of a $VB_{12}$, cyanocobolamine with chloro, sulphate, nitro, thio or its analide, ethylamide propionamide, monocarboxylic and dicarboxylic acid derivatives of a $VB_{12}$ or its analog, monocarboxylic, dicarboxylic and tricarboxylic acid derivatives and prominamide derivatives of 'e' isomer of monocarboxy $VB_{12}$, and analogues of $VB_{12}$ in which cobalt is replaced by other metals.

6. A complex as claimed in claim 1, wherein said one or more spacers link the primary 5'-hydroxyl and/or 2'-hydroxyl of the ribose moiety of the derivative of $VB_{12}$ to said particulate carrier.

7. A complex as claimed in claim 1, wherein said spacer is the residue after linking of a compound selected from the group consisting of diacids (COOH—COOH), alkyl diacids (COO($CH_2$)nCOO)), alkyl diamines ($NH_2$($CH_2$)n—$NH_2$), alkyl diamides (NHCO (CH)nCONH$_2$), hydrazides ($NH_2NH_2$), alkyl dihydrazides ($NH_2$NHCO($CH_2$) nCONHNH$_2$, SH group containing agents (N-succinymidyl$_3$-(2-pyridyidithio), propionate or its long chain alkyl derivatives or acid anhydrides [(CH)nCOCOO)], acid halide spacers (R($CH_2$)nCOCl), and anhydroxy activated ester functional groups (NHS) which are used for the peptide bonds or surfactant derivatives or polymeric spacers.

8. A complex as claimed in claim 1 wherein, the microspheres or nanoparticles are made up of biodegradable and pharmaceutically acceptable polymers.

9. A complex as claimed in claim 1 wherein, the drug loaded polymeric particulates degrade in-vivo to release and deliver a protein pharmaceutical/vaccine for its bioactive response.

10. A complex as claimed in claim 1, wherein said particulate carrier is a biodegradable hydrophobic or hydrophilic polymeric microsphere or nanoparticle having one or more functional groups selected from the group consisting of COOH, anhydride, $NH_2$ and SH groups on its surface which are used for linkage to said spacer.

11. A complex as claimed in claim 1, wherein said particulate carrier is a monolithic particle, reservoir particle, multi particulate particle, or conjugate polymer particle.

12. A complex as claimed in claim 1, wherein said particulate carrier comprises a polysaccharide polymer selected from the group consisting of starch and its derivatives, pectin, amylose, guar gum and its derivatives, dextran and its derivatives, chitosan and its derivatives, chondroitin sulphate and its derivatives, and the natural and semi-synthetic derivatives of polysaccharides.

13. A complex as claimed in claim 12, wherein said polysaccharide is crosslinked with an agent selected from the group consisting of epichlorohydrin, $POCl_3$, borax, and aldehydes.

14. A complex as claimed in claim 10, wherein said biodegradable polymer is selected from the group consisting of poly(methylmethacrylate), poly(hydroxybutyrate), polylactide(coglycolic acid), poly(anhydride) microspheres of (fumaric acid:sebacic acid), poly (fumaric acid), poly (lactide co-glycolide), fatty acylated particulates, LDL carriers, and multiparticulate systems.

15. A complex as claimed in claim 1, wherein said particulate carrier further comprises a natural protein polymer selected from the group consisting of albumin, gelatin, a semi synthetic or peptide based synthetic polymer and their derivatives.

16. A complex as claimed in claim 1, wherein the size of said complex ranges from about a few nanometers to about 10 µm.

17. A complex as claimed in claim 1 wherein, these particulate systems which are modified or activated on the surface to suit $VB_{12}$ linkage and/or complexation.

18. A complex as claimed in claim 16 wherein, the particulate system is surface modified with $VB_{12}$ and includes coupling of $VB_{12}$ to biodegradable particulate carriers.

19. A complex as claimed in claim 16, wherein, coupling of $VB_{12}$ derivative and particulates include both biodegradable and non biodegradable bonds with and without spacers in between.

20. A complex as claimed in claim 1, wherein said $VB_{12}$ derivative and said particulate carrier are coupled by amide bond of a carbodiimide selected from the group consisting of 1-ethyl 3-3dimethyl amino propyl carbodiimide (EDAC), 1,1'carbonyl diimidazole (CDl), N,N'diisopropyl carbodiimide (DIPC), and other peptide coupling agents or N-hydroxy succinimide activated coupling (NHS) or periodate coupling or glutaraldehyde activated coupling or CNBR mediated coupling or acid halide induced amide coupling or by the use of hydrophilic spacer ethylene glycol bis (succinimidyl succinate) (EGS) or hydrophobic spacers disuccinimidyl suberate (DSS) or via a thiol cleavablespacer with N-succinimidyl 3-(2-pyridyidithio) propionate (SPDP).

21. A complex as claimed in claim 1 wherein, the coupling involves physical adsorptive type or complexation.

22. A complex as claimed in claim 1, wherein said drugs, therapeutic peptides and proteins, or vaccines are entrapped within the highly dense VB12 coupled biodegradable particulate carriers.

23. A complex as claimed in claim 1, wherein the loading step of said drugs, therapeutic proteins and peptides, and vaccines to said carrier is preformed during the preparation of said particle carrier, or during the coupling process between said particle carrier and said $VB_{12}$ derivative.

24. A complex as claimed in claim 22, wherein said drugs, therapeutic peptides and proteins, or vaccines are entrapped within said carrier before, after, or during the process of conjugation, adsorption, covalent coupling, ionic interaction or complexation between said carrier and said $VB_{12}$.

25. A complex as claimed in claim 1, wherein a surfactant, an aggregation minimizer, a protease inhibitor, or a permeation enhancer is added as an additive into said system.

26. A complex as claimed in claim 1, wherein said delivery system is co-administered with an exogenous intrinsic factor (IF) of $VB_{12}$.

27. A complex as claimed in claim 1, wherein said delivery system is formulated into a dosage form suitable for oral delivery.

28. A complex as claimed in claim 27, wherein said oral dosage form is solution, suspension, gel, paste, elixir, viscous colloidal dispersion, tablet, capsule, or oral control release type.

29. A complex as claimed in claim 1, wherein said therapeutic peptides and proteins are selected from the group consisting of insulin, EPO, G-CSF, GM-CSF, Factor VIII, LHRH analogues and Interferons.

30. A complex as claimed in claim 1, wherein, said vaccines are selected from the group consisting of Hepatitis 'B' surface antigen vaccine, typhoid vaccine and cholera vaccine.

31. A method of modifying a micro or nano particle carrier for delivery of injectable drugs, therapeutic proteins and peptides, or vaccines to make it suitable for oral delivery, the method comprising coupling to said carrier a Vitamin $B_{12}$ to form a complex as claimed in claim 1.

* * * * *